US011946834B1

(12) United States Patent
Junghans et al.

(10) Patent No.: US 11,946,834 B1
(45) Date of Patent: Apr. 2, 2024

(54) HIGH EFFICIENCY ACTIVE ENVIRONMENTAL SAMPLING OF CHEMICAL TRACES

(71) Applicant: Triad National Security, LLC, Los Alamos, NM (US)

(72) Inventors: Ann Junghans, Los Alamos, NM (US); Eric Davis, Los Alamos, NM (US); Cristian Pantea, Los Alamos, NM (US); Rollin Lakis, Los Alamos, NM (US); Vlad Henzl, Los Alamos, NM (US)

(73) Assignee: TRIAD NATIONAL SECURITY, LLC, Los Alamos, NM (US)

( * ) Notice: Subject to any disclaimer, the term of this patent is extended or adjusted under 35 U.S.C. 154(b) by 66 days.

(21) Appl. No.: 17/514,945

(22) Filed: Oct. 29, 2021

Related U.S. Application Data

(60) Provisional application No. 63/108,061, filed on Oct. 30, 2020.

(51) Int. Cl.

| | |
|---|---|
| ***G01N 1/00*** | (2006.01) |
| ***G01N 1/04*** | (2006.01) |
| ***G01N 1/36*** | (2006.01) |
| ***G01N 1/40*** | (2006.01) |
| ***G01N 21/65*** | (2006.01) |
| ***G01N 33/22*** | (2006.01) |
| *G01N 1/02* | (2006.01) |

(52) U.S. Cl.

CPC ................. *G01N 1/04* (2013.01); *G01N 1/36* (2013.01); *G01N 1/4077* (2013.01); *G01N 21/658* (2013.01); *G01N 33/227* (2013.01); *G01N 2001/028* (2013.01); *G01N 2001/4094* (2013.01)

(58) Field of Classification Search

None

See application file for complete search history.

(56) References Cited

U.S. PATENT DOCUMENTS

| | | |
|---|---|---|
| 3,023,122 A | 2/1962 | De Pataky |
| 8,658,580 B2 | 2/2014 | Kaminski et al. |

(Continued)

OTHER PUBLICATIONS

Almaviva, S. et al., "Trace Detection of Explosives and Their Precursors by Surface Enhanced Raman Spectroscopy," *Proc. SPIE 8546, Optics and Photonics for Counterterrorism, Crime Fighting, and Defence VIII*, 2012, 854602, 7 pages.

(Continued)

*Primary Examiner* — Jyoti Nagpaul

(74) *Attorney, Agent, or Firm* — Lewis Roca Rothgerber Christie LLP

(57) ABSTRACT

A method of sample collection includes collecting an analyte from a sampling surface using a rapidly curable liquid gel comprising one or more metal particles; co-aggregating the one or more metal particles from the rapidly curable liquid gel and the analyte from the sampling surface; and rapidly curing the rapidly curable liquid gel. The composition and sample preparation conditions may facilitate improved collection efficiency of analytes during environmental and forensic evidence sampling. In addition, the composition and sample preparation conditions may facilitate enhanced detection and identification of the analyte using e.g., Surface Enhanced Raman Spectrometry (SERS).

18 Claims, 14 Drawing Sheets

(56) References Cited

U.S. PATENT DOCUMENTS

| | | | | |
|---|---|---|---|---|
| 10,883,901 | B1 * | 1/2021 | Henzl | B01J 20/286 |
| 2005/0230267 | A1 | 10/2005 | Veatch et al. | |
| 2014/0274660 | A1 | 9/2014 | Kabir et al. | |
| 2015/0240115 | A1 | 8/2015 | Larsen et al. | |
| 2016/0202149 | A1 | 7/2016 | Thomson et al. | |

OTHER PUBLICATIONS

Andrade, M. et al., "Particle manipulation by a non-resonant acoustic levitator," *Appl. Phys. Lett.*, 2015, 106, 014101, 10 pages.

Du, Y. et al., "Surface-Enhanced Raman Scattering Chip for Femtomolar Detection of Mercuric Ion (II) by Ligand Exchange," *Analytical Chemistry*, 2013, 85(6), 3160-3165.

Grineko, A. et al., "Efficient counter-propagating wave acoustic micro-particle manipulation," *Appl. Phys. Lett.*, 2012, 101, 233501, 4 pages.

Hong, S & Li, X, "Optimal Size of Gold Nanoparticles for Surface-Enhanced Raman Spectroscopy Under Different Conditions," *Journal of Nanomaterials*, 2013, 1-9.

Hu, Fei, et al., "Smart Liquid SERS Substrates based on Fe3O4/Au Nanoparticles with Reversibly Tunable Enhancement Factor for Practical Quantitative Detection", Scientific Reports (2014), 4:7204, DOI: 10.1038, pp. 1-10.

Jimenez-Sandoval, S., "Micro-Raman spectroscopy: a powerful technique for materials research", Microelectronics Journal (2000) 3:419-427.

Kaduchak, G., et al., "Acoustic Aerosol Concentration and Particle Manipulation," *LA-UR-04-110*, LANL Library Catalog, ID:01LANL_ALMA51100412370003761, 23 pages.

Kale, A. et al., "An improved model for acoustic particle concentration—A case study in piezo-tubes," *2018 IEEE 18th International Conference on Nanotechnology* (*IEEE-NANO*), Cork, Ireland, 2018, pp. 420-425.

Kogan, S. et al., "Acoustic concentration of particles in piezoelectric tubes: Theoretical modeling of the effect of cavity shape and symmetry breaking," *Journal of the Acoustical Society of America*, 2004, 116, 1967.

Lee, Sangmin, et al., "Light Output of Plastic Scintillators Fabricated by UV Curling", Transactions of the Korean Nuclear Society Spring Meeting, Jeju, Korea, May 18-19, 2017, 3 pps.

Li, Y. et al., "Raman tags: Novel optical probes for intracellular sensing and imaging," Biotechnology Advances, 2017, 3, 168-177.

Synytsya, A. et al., "Raman spectroscopy at different excitation wavelengths (1064, 785 and 532 nm) as a tool for diagnosis of colon cancer," *Journal of Raman Spectroscopy*, 2014, 45(10), 903-911.

Wang, K. et al., "Detection and Characterization of Antibiotic-Resistant Bacteria Using Surface-Enhanced Raman Spectroscopy," *Nanomaterials*, 2018, 8(10), 762, 21 pages.

Wang, T. et al., "Particle manipulation with acoustic vortex beam induced by a brass plate with spiral shape structure," *Appl. Phys. Lett.*, 2016, 109, 123506.

Zhu, Jun , et al., "Preparation and characterization of a novel UV-curable plastic scintillator", Nuclear Instruments and Methods in Physics Research A (2016) 828:30-34.

* cited by examiner

Approx. 0% Removal

HIGH EFFICIENCY ACTIVE ENVIRONMENTAL SAMPLING OF CHEMICAL TRACES

CROSS-REFERENCE TO RELATED APPLICATIONS

The present application claims priority to and the benefit of U.S. Provisional Application No. 63/108,061, filed Oct. 30, 2020, entitled "HIGH EFFICIENCY ACTIVE ENVIRONMENTAL SAMPLING OF CHEMICAL TRACES," the entire content of which is incorporated herein by reference.

This application may be related to U.S. application Ser. No. 15/785,295, filed Oct. 16, 2017 and titled "HIGH EFFICIENCY ENVIRONMENTAL SAMPLING WITH RAPIDLY CURED PEELABLE COATINGS," which claims priority to and the benefit of U.S. Provisional Application No. 62/408,589, filed Oct. 14, 2016 and titled "HIGH EFFICIENCY ENVIRONMENTAL SAMPLING WITH RAPIDLY CURED PEELABLE COATINGS," the entire content of each of which is incorporated herein by reference.

STATEMENT REGARDING GOVERNMENT RIGHTS

The United States government has rights in this invention pursuant to Contract No. 89233218CNA000001 between the United States Department of Energy/National Nuclear Security Administration and Triad National Security, LLC for the operation of Los Alamos National Laboratory.

BACKGROUND

Environmental and forensic evidence sampling is often performed using glue paper or cotton swipes or swabs to mechanically collect analytes from surfaces. The collection efficiency of such swipes or swabs is typically low (about 10% to less than 1% of the total environmental presence of the analyte), and strongly depends on the chemical and physical properties of the analyte as well as the structure of the surface from which the sample is collected. For example, the collection efficiency by cotton swipes of analytes embedded in surfaces of porous materials such as wood, concrete, or fabric is substantially or practically zero. Furthermore, analytes collected by cotton swipe or swab are susceptible to being shaken off the loose cotton matrix during transport and/or storage, resulting in further loss (typically about 10 percent or more of the total collected amount) of the analyte. Additionally, environmental and operator variations in swiping technique may contribute to data that is difficult to quantitate and reproduce. Accordingly, existing cotton swipe and swab based sample collection techniques and materials are often unsatisfactory for accurate and sensitive detection of trace amounts of chemical, biological, radiological, nuclear, or explosive (CBRNE) material, and are generally not suitable for preserving forensic evidence.

SUMMARY

According to embodiments of the present disclosure, a method includes applying a rapidly curable liquid gel having one or more metal particles to a sampling surface, co-aggregating the one or more metal particles in the rapidly curable liquid gel and an analyte from the sampling surface by applying ultrasonic waves to the rapidly curable liquid gel and the underlying sampling surface, curing the rapidly curable liquid gel to yield a sampling matrix including the analyte, and removing the sampling matrix including the analyte from the sampling surface.

In some embodiments, curing the rapidly curable liquid gel is at least partially concurrent with co-aggregating the one or more metal particles and the analyte.

According to some embodiments, applying ultrasonic waves to the rapidly curable liquid gel and underlying sampling surface includes using a piezoelectric transducer. In some embodiments, the piezoelectric transducer may include a hollow tube and generate ultrasonic waves in a radial direction inside the hollow tube.

In some embodiments, the one or more metal particles may have an average size of about 1 nm to about 400 nm. And in some embodiments, the one or more metal particles may include gold (Au), silver (Ag), or any combination thereof. In some embodiments, the one or more metal particles may include metal nanoparticles or metal nanostructures. And in some embodiments, the concentration of the one or more metal particles in the rapidly curable liquid gel may be about 0.001 wt % to about 10 wt % with respect to the total weight of the rapidly curable liquid gel.

According to some embodiments, the rapidly curable liquid gel may further include a Raman probe to co-localize with the one or more metal particles and/or the analyte. And in some embodiments, the rapidly curable liquid gel may further include a Raman probe to associate with and quench the analyte. In some embodiments, the rapidly curable liquid gel may further include a Raman probe that is quenched in the presence of the analyte.

In some embodiments, curing the rapidly curable liquid gel may include using a portable energy source to deliver energy suitable to cure the rapidly curable liquid gel.

In some embodiments, the method may further include measuring a Raman intensity of the analyte from the sampling matrix removed from the sampling surface. And in some embodiments, measuring the Raman intensity of the analyte may include using a handheld Raman device.

According to some embodiments, a method includes applying a rapidly curable liquid gel to a sampling surface, aggregating an analyte of the sampling surface by applying ultrasonic waves to the rapidly curable liquid gel and the underlying sampling surface, curing the rapidly curable liquid gel to yield a sampling matrix including the analyte, and removing the sampling matrix including the analyte from the sampling surface.

In some embodiments, applying ultrasonic waves to the rapidly curable gel and the sampling surface may include using a piezoelectric transducer. And in some embodiments, the piezoelectric transducer may include a hollow tube and generate ultrasonic waves in a radial direction inside the hollow tube.

According to some embodiments, curing the rapidly curable liquid gel comprises using a portable energy source to deliver energy suitable to cure the rapidly curable liquid gel.

In some embodiments, the method may further include measuring a Raman intensity of the analyte from the sampling matrix removed from the sampling surface. And in some embodiments, measuring the Raman intensity of the analyte may include using a handheld Raman device.

BRIEF DESCRIPTION OF THE DRAWINGS

These and other features and advantages of embodiments of the present disclosure will be better understood by reference to the following detailed description when considered in conjunction with the accompanying drawings, in which.

DETAILED DESCRIPTION

Figure 1A:
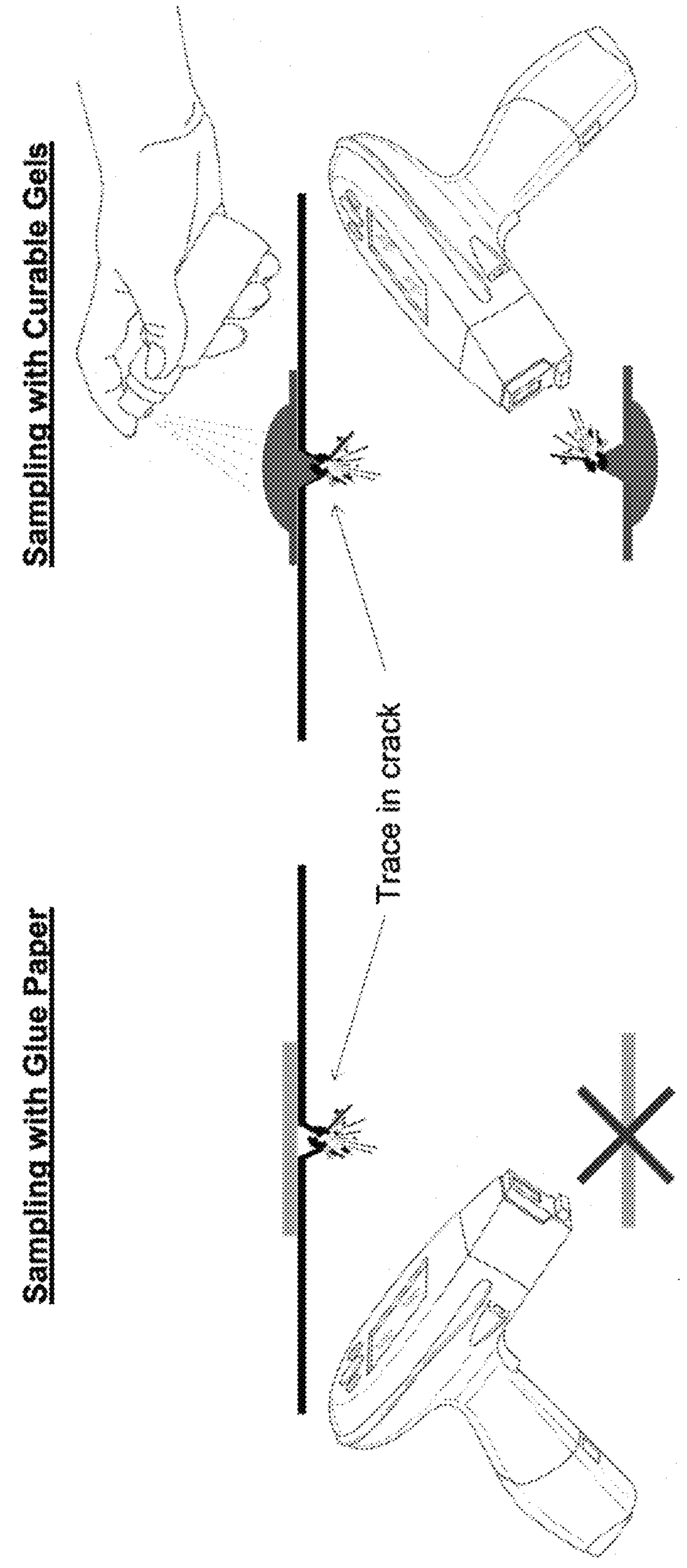
FIG. 1A is a schematic illustration comparing analyte sampling (collection) from a surface containing a trace high explosive (HE) sample embedded in a crack in the surface, using conventional glue paper (left) and using the rapidly curable liquid gel according to embodiments of the present disclosure (right)

Aspects of example embodiments of the present disclosure are directed toward collecting an analyte from a sampling surface, including methods, compositions, devices, and kits to facilitate analyte collection. Embodiments may include a rapidly curable liquid gel including metal particles, which is converted into a polymeric sampling matrix (e.g., a solidified layer of polymer gel having any suitable thickness) during and/or after aggregation (co-aggregation) of the metal particles and the analyte. The particles may be co-aggregated by any suitable technique, some non-limiting examples of which include applying a magnetic or electromagnetic field, applying an ultrasonic field, applying a current, by self-assembly, etc. In some embodiments, for example, the metal particles and analyte may be co-aggregated by application of ultrasonic waves to the rapidly curable liquid gel.

The methods, compositions, devices, and kits described herein may facilitate an increase in analyte collection efficiency and reproducibility, compared to conventional cotton swipes, swabs, and other sampling glues or films in the art. For example, a rapidly curable liquid gel optionally containing additives to enhance solubility, collection, and/or detection of suspected analytes may be applied to a sampling surface and cured in situ to thereby produce a sampling matrix containing the embedded analytes. The embedded analytes can then be identified and/or quantified using any suitable technique.

In addition, the composition and sample preparation conditions according to embodiments of the present disclosure may facilitate enhanced detection and identification of the analyte using e.g., Surface Enhanced Raman Spectrometry (SERS), which is a non-destructive detection method capable of assaying Raman-active molecules, including many narcotic and explosive agents. SERS takes advantage of an electromagnetic interaction between the assaying laser and metal particles included in a sample, which may enhance Raman scattering and spectral response of co-existing analyte molecules by a factor of about $10^5$ to $10^{14}$. For example, the methods and compositions described herein may enable co-aggregation (co-localization) of analyte particles and metal particles within particular regions of the cured liquid gel, which can then provide enhanced Raman signals due to increased local concentrations of the analyte, in combination with signal amplification by the metal particles.

Additional methods for enhancing analyte collection by (and concentration within) the polymeric sampling matrix may enable improved analyte sampling and analysis (for example, using SERS) with increased accuracy, sensitivity, and/or reproducibility.

The rapidly curable liquid gel may be used to form a sampling matrix. The term "sampling matrix" as used herein may refer to a polymer matrix used to collect an analyte material, as used in e.g., environmental and forensic sampling. The rapidly curable liquid gel may be directly applied to and polymerized on a surface containing the analyte material, so that the analyte may first dissolve and/or be suspended in the liquid gel, and subsequently be embedded in, absorbed in, adsorbed to, and/or trapped by the resulting sampling matrix. The rapidly curable liquid gel may be able to seep into porous or microtextured surfaces to retrieve more analyte therein, and can be applied in a reproducible manner. The polymeric sampling matrix can then act as a stable matrix to securely hold the analyte. In addition, the flexibility and tensile strength of the sampling matrix may allow for consistent separation (e.g., by peeling) of the matrix from the sampling surface. Accordingly, the polymeric sampling matrices according to embodiments of the present disclosure may provide improved analyte collection efficiencies, compared to non-polymer methods. The sampling matrix may have any suitable thickness and area (size), as determined by the amount and application area of the rapidly curable liquid gel on the sampling surface.

The term "rapidly curable liquid gel" as used herein may refer to a liquid material, mixture, or composition that can be converted to a solid material within an amount of time suitable for efficient and effective sample collection (e.g., a timescale of a few seconds to a few minutes, and in some embodiments less than one minute). For example, the rapidly curable liquid gel may be applied to a surface including an analyte, may dissolve or suspend the analyte, and may then be rapidly cured to form a sampling matrix containing the analyte. Once the analyte is captured within the sampling matrix, the analyte may be detected, analyzed, identified, and/or quantified using any suitable technique. In some embodiments, the analyte may be analyzed using Raman spectroscopy.

Raman spectroscopy is a non-destructive characterization technique that uses the inelastic scattering of monochromatic light to detect molecules based on their vibrational modes. Briefly, a molecule (or moiety) is Raman active (e.g., shows a Raman shift) when irradiation with light causes a change in the molecule's polarizability (a), accompanied by scattering of the photon with a different frequency. The collection of Raman shifts (e.g., shift in frequency of the scattered and detected photons, compared to the irradiated photons), when plotted as a spectrum, provides a "molecular fingerprint" that can be used to identify the molecule.

The intensity of a particular Raman shift is proportional to the change in polarizability ($\alpha$), but the overall intensity of the spectrum and resultant potential to detect a particular molecule may be limited by low or insufficient sample concentrations. Furthermore, the signal to noise (S/N) ratio of the Raman spectrum may be low due to the background fluorescence (signal) produced by some polymers within the sampling matrix, even when background subtraction methods are applied to the data. Accordingly, techniques for selectively enhancing the signal from analyte samples having relatively low concentrations (such as trace amounts of a molecule present in a forensic evidence sampling scenario) are desired.

Surface Enhanced Raman Spectrometry (SERS) is a variation of Raman spectroscopy that takes advantage of a signal enhancement effect that occurs when Raman-active molecules are adsorbed on or positioned near a metal surface having a nanostructured texture. Without being bound by the correctness of any theory or explanation, it is thought that surface plasmons (evanescent waves) generated during irradiation of the metal surface enhance the electric field at that surface, which in turn magnifies the intensities of irradiated and scattered photons that interact with the electric field. Alternatively or in addition, it is thought that formation of charge transfer complexes between the metal surface and molecules of interest may enhance Raman scattering, as described, for example, in Wang, K. et al., "Detection and characterization of antibiotic-resistant bacteria using surface-enhanced raman spectroscopy," *Nanomaterials,* 2018, 8(10), 762, the entire content of which is incorporated herein by reference. The intensity of the Raman-detected photons may therefore be enhanced during both irradiation and scattering, resulting in signal increase by a factor of about $10^5$ to $10^{14}$. SERS may be performed on molecules at planar metal surfaces or in the presence of metal particles. In the case where SERS is performed on a sampling matrix produced from a rapidly curable liquid gel (as described in more detail below), metal particles capable of enhancing the SERS signal may be included within the liquid gel and resulting sampling matrix.

Because the SERS laser (which typically has wavelengths in the ultraviolet (UV) to near infrared (NIR) spectral ranges) may not be able to penetrate through the sampling matrix, sample analysis may be limited to the molecules and metal particles at or within a few nm or mm of the surface sampling matrix. Moreover, the fluorescent background signal associated with the sampling matrix may obscure signals from low-concentration analytes. Furthermore, additional signal enhancement beyond that afforded by the use of the SERS technique may be desired. The complementary utilization of ultrasonic waves and other aggregation methods according to embodiments of the present disclosure may facilitate additional improvements in sample collection and analysis by: 1) enhancing dissolution and/or suspension of the analyte in the rapidly curable liquid gel and resulting sampling matrix; and 2) concentrating and/or co-aggregating the analyte and metal particles within set, predetermined, or controllable regions of high concentration near the surface of the sampling matrix. Such regions of high concentration can then be analyzed with any suitable technique (including SERS) at increased detection levels.

As used herein, the terms "aggregation" and "co-aggregation" both refer to the process of aggregating particulates within the rapidly curable liquid gel. However, the term "aggregation" refers to the aggregation of a single species, e.g., the metal particles or the Raman active material (e.g., the analyte) within the rapidly curable liquid gel, while the term "co-aggregation" refers to the simultaneous or concurrent aggregation of more than one species, e.g., the metal particles and the analyte within the rapidly cured liquid gel. Also, while aggregation of the metal particles (or the analyte), or co-aggregation of the metal particles and the analyte, refers to the collection (or aggregation) of the particles within a particular field (generally defined by the application of energy), aggregation and co-aggregation do not require or intimate that the particles (whether metal particles, analyte, or metal particles and analyte) must be in physical contact. Rather, aggregation and co-aggregation refers to the creation (or definition) of a field defined in area by the metal particles (or analyte), and that the analyte is within the vicinity of that field.

As used herein, the term "high concentration" may refer to any concentration higher (for example, at least 10% higher, or at least 25% higher) than the average concentration per area that would be provided if the analyte were evenly distributed over the surface area of the sampling matrix. In some embodiments, "high concentration" may refer to any concentration capable of being detected by a suitable detection or analysis technique, such as SERS.

The terms "ultrasonic," "sonic," "sound," "acoustic," and like terms used interchangeably herein may refer to transmission of mechanical pressure waves (including audible, sub-audible, ultrasound, and/or the like) through air, liquid, and/or semi-liquid media. The term "semi-liquid" used herein may refer to a material capable of limited or reduced flowing, as compared to a liquid such as water, and for example, may refer to a curable liquid gel in an intermediate curing state.

The terms "analyte," "analytes," "samples," and like terms used interchangeably herein may refer to any substance of interest that can be trapped, embedded, or otherwise captured in the rapidly curable liquid gel. The analyte may be in any suitable form or size, and for example, may be referred to as being particles or molecules depending on whether the analyte is suspended or dissolved, respectively, in the rapidly curable liquid gel. The analyte may be a chemical, biological, radiological, nuclear, or explosive (CBRNE) sample; however, the analyte is not limited to these categories.

As used herein, the term "chemical sample(s)" and like terms may refer to any non-biological material that is to be quantified or identified based on its elemental composition, molecular structure, chemical properties, chemical reactivity, or reaction to electromagnetic energy stimuli or input (e.g., chemical spectra). Non-limiting examples of chemical samples include organic or inorganic substances, for example, gun powder and gunshot residues, physiologically active and psychoactive substances (e.g., drugs, poisons, and pharmaceuticals), chemical warfare agents, hydrocarbons and fire accelerants, paint, polymer, and plastic particles, fibers, dirt, adhesives, heavy metals, etc.

As used herein, the term "biological sample(s)" and like terms may refer to any material of biological origin or material that is produced within a biological system, such as a plant, animal, microorganism, or cell. Non-limiting examples of biological samples include biotoxins, fingerprints, tissues (such as skin and hair), residue from fluids (such as saliva, blood, and semen), nucleic acid polymers (such as DNA and/or RNA), proteins, lipids, microorganisms and microflora (such as bacteria, viruses, and fungi), and cells (e.g., mammalian cells).

As used herein, the terms "radiological sample(s)," "nuclear sample(s)," "nuclear contaminants," and like terms may refer to any material that emits ionizing radiation, includes atoms or nuclear isotopes exhibiting radioactivity, or otherwise spontaneously undergoes nuclear decay. The material may be a compound, such as a fluoride, oxide, or nitrate of the atom or nuclear isotope. Non-limiting examples of such atoms include isotopes of uranium (U), plutonium (Pu), thorium (Th), and the like. The sizes and shapes of nuclear contaminants are not particularly limited, and may include particles having millimeter or micron scale diameters. The type of radiation emitted by the nuclear contaminants may include alpha-, beta-, gamma-, and neutron-radiation.

As used herein, the term "explosive samples" and like terms may refer to any material storing a large amount of potential energy that, upon a stimulus (such as heat, spark, friction, and/or impact) suddenly releases the energy in the form of light, heat, sound, and/or pressure. Non-limiting examples of explosive samples include nitro-group containing organic compounds (such as nitroglycerin, TNT, DNT, PETN, RDX, HMX, HMTD, TATP, nitrourea, octogen, picric acid, nitrocellulose, etc.), azide-containing compounds (such as sodium azide, lead azide, barium azide, 2-dimethylaminoethylazide, etc.), nitrate-containing compounds (such as sodium nitrate, calcium nitrate, ammonium nitrate, etc.), peroxides, perchlorates, and mixtures such as blasting powder, etc.

As used herein, the term "substantially" is used as a term of approximation and not as a term of degree, and is intended to account for the inherent inaccuracies in measured, observed, or calculated values or qualities. For example, the term "substantially zero" as used herein to refer to the sampling efficiency of a cotton swipe on a porous material means that the sampling efficiency is so low that the detectable amount of analyte is effectively indistinguishable from a negative control (e.g., the absence of the analyte).

Many CBRNE threat agents, including high explosives, organo-phosphorus nerve agents, and biological pathogens (such as *Bacillus anthracis*) have or include molecular structures that are potentially Raman active and can be identified using the above-described "molecular fingerprint" method. However, such detection may be limited by low available concentrations of the threat agent analyte. Accurate detection and identification of exceedingly trace amounts of such threat agents, in the field and in real time, is a critical need for first responders, military, and law enforcement. The methods, compositions, devices, and kits according to embodiments of the present disclosure meet this critical need by being highly compatible with rapid, portable detection of such analytes in trace amounts.

According to one or more embodiments of the present disclosure, a kit for collecting an analyte from a sampling surface includes: a rapidly curable liquid gel comprising one or more metal particles; a source of energy for application to the rapidly curable liquid gel configured to deliver energy suitable to promote or cause co-aggregation of the metal particles in the rapidly curable gel and the analyte from the sampling surface; and a portable device configured to enable rapid curing of the rapidly curable liquid gel. The energy delivered or provided by the source of energy is not particularly limited, and may include electromagnetic, magnetic, or acousto-mechanical energy. In some embodiments, for example, the source of energy may be a piezoelectric transducer, as described herein.

The rapidly curable liquid gel and aspects of methods of using the rapidly curable liquid gel may be substantially the same as described in U.S. application Ser. No. 15/785,295, filed Oct. 16, 2017 and titled "HIGH EFFICIENCY ENVIRONMENTAL SAMPLING WITH RAPIDLY CURED PEELABLE COATINGS," the entire content of which is incorporated herein by reference. For example, the rapidly curable liquid gel may include a polymer precursor mixture comprising one or more monomers or oligomers capable of crosslinking on exposure to UV light. Stated another way, the rapidly curable liquid gel may be UV curable. In some embodiments, the rapidly curable liquid gel may include urethane- and acrylate-based monomers to thereby provide a crosslinked urethane acrylate polymer.

The metal particles included in the rapidly curable liquid gel may include or be formed of any material (e.g., any metal) capable of producing surface plasmons at Raman laser frequencies. In some embodiments, the metal particles may include or be formed of gold (Au), silver (Ag), copper (Cu), platinum (Pt), palladium (Pd), aluminum (Al), or any combination thereof. In some embodiments, the metal particles may include or be formed of Au or Ag, and in some example embodiments, the metal particles may include or be formed of Au.

The metal particles may be any suitable size and shape, without limitation, as long as the particles can be included in the rapidly curable liquid gel without interfering with gel application (e.g., even flow and spreading of the liquid gel onto a sampling surface) or the removal (e.g., consistent, unbroken peeling) of the resultant sampling matrix. Furthermore, the size, shape, and dimensions of the metal particles may be selected according to their effect on Raman scattering enhancement. For example, the size of the metal particles may be selected to maintain the electrical conductance of the substrate while minimizing the excitation of non-radiative vibrational or rotational transitions. As another example, the size and shape of the metal particles may be selected to modify the plasmon oscillation frequency, e.g., to match lower excitation wavelengths that may be able to better penetrate the rapidly curable liquid gel and sampling matrix, or for example, to match excitation wavelengths that enhance signal from the analyte while reducing or minimizing the background fluorescence of the sampling matrix. Discussions of the relationship between particle size, excitation wavelength, and spectral results can be found in e.g., Synytsya, A. et al., "Raman spectroscopy at different excitation wavelengths (1064, 785 and 532 nm) as a tool for diagnosis of colon cancer," *Journal of Raman Spectroscopy,* 2014, 45(10), 903-911 and Hong, S & Li, X, "Optimal size of gold nanoparticles for surface-enhanced Raman spectroscopy under different conditions," *Journal of Nanomaterials,* 2013, 1-9, the entire content of each of which is incorporated herein by reference.

In some embodiments, the metal particles may have an average diameter (also interchangeably referred to herein as "particle size" or "average particle size") of about 1 nm to about 500 nm, about 2 nm to 400 nm, about 5 nm to about 300 nm, or about 10 nm to about 200 nm. In some embodiments, the metal particles may have an average diameter of about 1 nm to about 100 nm, or about 5 nm to about 50 nm.

In some embodiments, the metal particles may be or include nanoparticles or nanoconfined structures. As used herein, the term "nanoparticles" may refer to particles having an average diameter (average size) on the scale of a few to tens of nanometers (nm), for example, having an average diameter of less than about 100 nm, such that all particle dimensions are within this scale. As used herein, the terms "nanostructures," and/or "nanoconfined structures" may refer more generally to particles or other structures having at least one dimension on the scale of a few to tens of nanometers (nm), for example, having at least one dimension with an average length of less than about 100 nm. The remaining dimensions may also be on this scale, or in some embodiments may be larger. For example, the nanoconfined structures may have one such dimension on the above scale (e.g., may be one-dimensional nanostructures); may have two such dimensions on the above scale (e.g., may be two-dimensional nanostructures); and in some embodiments may have three such dimensions on the above scale (e.g., may be three-dimensional nanostructures, also referred to as nanoparticles).

Non-limiting examples of the nanoconfined structures may include one-dimensional structures such as nanoplates and nanosheets, two-dimensional structures such as nanorods and nanopillars, and three-dimensional structures such as nanoparticles, nanospheres, nanocages, etc. Any suitable method in the art for preparing such nanoconfined structures may be used. In some embodiments, the nanoconfined structures may form nanoclusters.

In some embodiments, when the metal particles are nanoparticles, the nanoparticles may be solid nanoparticles having a constant (fixed) composition throughout the particle. In some embodiments, the nanoparticles may have compositional gradients or spatial variations in composition. In some embodiments, for example, the nanoparticles may be core-shell nanoparticles, where the outer shell is formed of a metal material that produces surface plasmons, and the core may be formed of any suitable material available in the art (and is not necessarily capable of producing surface plasmons). In some embodiments, the core may be a dielectric material. For example, the core may be formed of silica, alumina, etc. In some embodiments, the nanoparticles may be hollow nanoshells, where the shell is formed of the metal material that produces surface plasmons, and no core is present.

In some embodiments, for example when it is desirable to minimize possible exposure to nanoparticles, the metal particles may be on a micron scale. For example, the metal particles may be about 100 nm to about 500 nm in each dimension (direction). In some embodiments, the metal particle may have an average diameter of about 100 nm to about 500 nm, about 150 nm to about 400 nm, or about 200 nm to about 300 nm.

The concentration of metal particles in the rapidly curable liquid gel may be selected, in accordance with the size and shape of the metal particles, to facilitate an improvement in SERS analysis by increasing the total surface area of the metal particles that is simultaneously co-aggregated (e.g., brought into proximity (but not necessarily in contact), or in contact) with the analyte and exposed to SERS radiation.

Further, in some embodiments, the concentration of metal particles may be high enough so that the metal particles can be physically adjacent and/or form a continuous network in at least some portions of the rapidly curable liquid gel and resulting sampling matrix, thereby enabling Raman enhancement "hot spots" due to cumulative interactions between analyte and neighboring metal particles.

In some embodiments, the concentration of the metal particles in the rapidly curable liquid gel may be about 0.001 wt % to about 10 wt % with respect to the total weight of the rapidly curable liquid gel, for example, about 0.01 wt % to about 5 wt %, about wt % to about 1 wt %, or about 0.1 wt % to about 0.5 wt %.

While embodiments of the present disclosure have been described as including metal particles, other embodiments may omit such metal particles. In some embodiments, for example, the rapidly curable liquid gel may be intended for a different analytical method than SERS, and may therefore not include or use metal particles to enhance a SERS response.

Embodiments of the present disclosure provide for applying a source of energy, for example in the form of electromagnetic, magnetic, or acousto-mechanical energy, to aggregate the metal particles in the rapidly curable gel (when present), or co-aggregate the metal particles along with the analyte from the sampling surface. The metal particles and/or analyte may be aggregated or co-aggregated using any suitable method(s) or source(s) of energy. Selected non-limiting examples include applying a magnetic field, applying an ultrasonic field, applying a current, by self-assembly, etc. Other suitable methods or phenomena, such as an electromagnetic field (as described in e.g., U.S. application Ser. No. 15/785,295 and U.S. Provisional Application No. 62/408,589, the entire content of each of which is incorporated herein by reference) may also be used.

In some embodiments, the source of energy comprises a piezoelectric transducer, and energy in the form of an ultrasonic field (e.g., acousto-mechanical energy) may be applied to aggregate or co-aggregate the metal particles and/or analyte. The ultrasonic field may be applied to the rapidly curable liquid gel to: 1) mechanically loosen analyte materials that may be adhered or adsorbed to the sampling surface, especially in cracks or other regions having textures and/or geometries that tend to enhance surface adsorption; and 2) concentrate and/or co-aggregate the analyte and the metal particles near the surface of the sampling matrix (e.g., near the interface of the sampling matrix with the sampling surface) and in particular regions, as will be described in more detail below. Each of these aims may be achieved via the application of ultrasonic waves, which are generated at the transducer and transmitted through the rapidly curable liquid gel. The ultrasonic waves may apply an acousto-mechanical force or pressure to the sampling surface and/or the rapidly curable liquid gel, which force or pressure may then be transferred to the analyte and/or metal particles to adjust their positions and distribution within the liquid or semi-liquid matrix of the rapidly curable liquid gel.

The pulse sequence, wave or beam shape, wave intensities, wave frequencies or frequency ranges, and/or directionality of the ultrasonic waves may be selected or controlled to improve or optimize one or both of the above-described aims. In some embodiments, a combination (e.g., series) of ultrasonic waves having forms that are independently optimized or suitable for either aim may be applied simultaneously or in sequence. The characteristics of the ultrasonic waves may be selected or determined by the form and structure of the piezoelectric transducer, described in more detail below.

In some embodiments, the ultrasonic waves may be or include resonant waves (e.g., ultrasonic waves having wavelengths coincident with the resonant modes of the piezoelectric transducer). The term "resonant wave" as used herein may refer to a standing or stationary waveform, for example, a wave with a fixed frequency and peak profile, which may be confined to a cavity e.g., within the piezoelectric transducer. When the ultrasonic waves are resonant waves applied substantially along or parallel to the sampling surface, the analyte and metal particles may be at least partially localized to regions corresponding to stationary nodes of the resonant wave.

In some embodiments, the ultrasonic waves may be or include non-resonant (traveling or longitudinal) waves. For example, the traveling waves may be used to vibrate and loosen particles on a sampling surface, or may be used to push an analyte and/or metal particle parallel to the direction(s) of wave propagation, and for example, towards particular (end) regions of the rapidly curable liquid gel. In some embodiments, two traveling waves propagating in opposite directions, or a traveling wave that is subsequently reflected back toward the analyte and/or metal particle may be used to manipulate the analyte and/or metal particle into arbitrary or selected intermediate positions.

Additional descriptions of transducers and devices for producing suitable ultrasonic waves can be found in e.g., Kale, A. et al., "An Improved Model for Acoustic Particle Concentration—A Case Study in Piezo-Tubes," 2018 IEEE 18th International Conference on Nanotechnology (IEEE-NANO), Cork, Ireland, 2018, pp. 420-425; Grinenko, A. et al., "Efficient counter-propagating wave acoustic micro-particle manipulation," *Appl. Phys. Lett.*, 2012, 101, 233501; Kogan, S. et al., "Acoustic concentration of particles in piezoelectric tubes: Theoretical modeling of the effect of cavity shape and symmetry breaking," Journal of the Acoustical Society of America, 2004, 116, 1967; "Acoustic Aerosol Concentration and Particle Manipulation," LA-UR-04-110, LANL Library Catalog, ID: 01LANL_ALMA51100412370003761; Andrade, M. et al., "Particle manipulation by a non-resonant acoustic levitator," Appl. Phys. Lett., 2015, 106, 014101; and Wang, T. et al., "Particle manipulation with acoustic vortex beam induced by a brass plate with spiral shape structure," *Appl. Phys. Lett.*, 2016, 109, 123506, the entire content of each of which is incorporated herein by reference.

The piezoelectric transducer may have any suitable shape and structure, which may be selected according to the desired characteristics of the ultrasonic waves that are produced by the transducer. The form and materials used for the piezoelectric transducer may also be selected to facilitate easy application and curing of the rapidly curable liquid gel. Stated another way, the form and materials used for the piezoelectric transducer should not inhibit or negatively impact the application and curing of the rapidly curable liquid gel on the sampling surface (including, e.g., the ability to irradiate the gel).

Figure 3A:
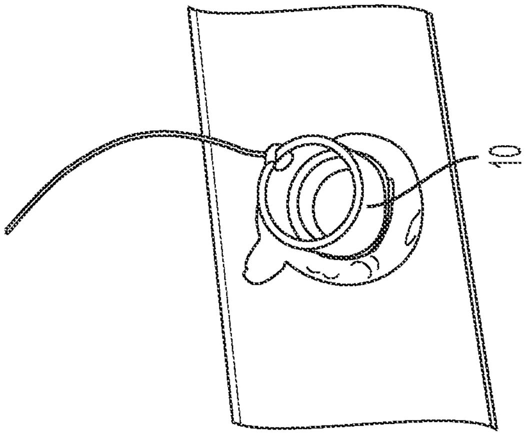
FIG. 3A is a schematic depicting an example transducer having the shape of a hollow cylinder placed against a surface to be sampled and filled with a rapidly curable liquid gel according to embodiments of the present disclosure.
Figure 3B:
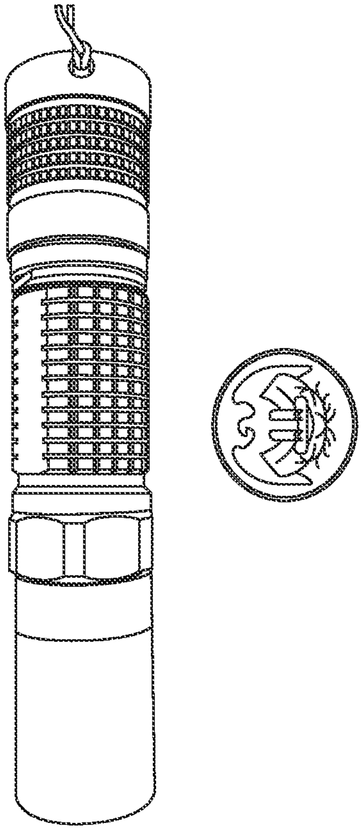
FIG. 3B is a schematic depicting a handheld UV lamp for curing the rapidly curable liquid gel in FIG. 3A.
Figure 3C:
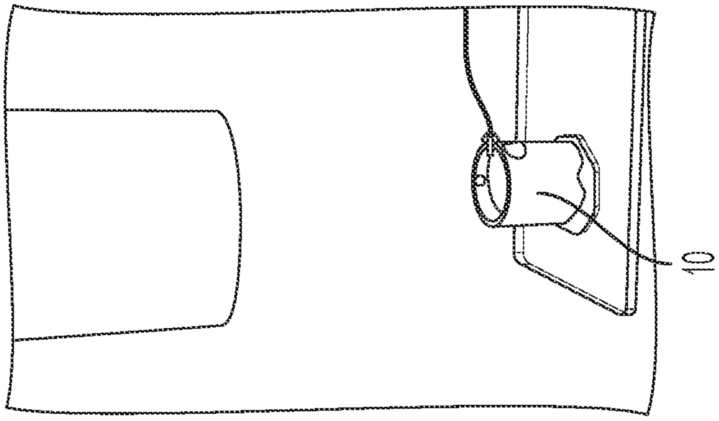
FIG. 3C is a schematic depicting the handheld UV lamp of FIG. 3B being used to cure the rapidly curable liquid gel contained within the transducer cavity of FIG. 3A.
Figure 3E:
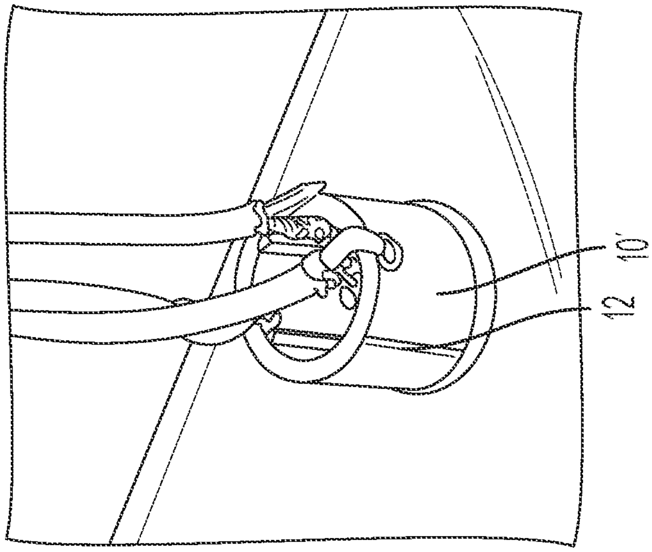
FIGS. 3D through 3G are schematics depicting example "split ring" transducers having the shape of a hollow cylinder with breaks according to embodiments of the present disclosure.
Figure 3D:
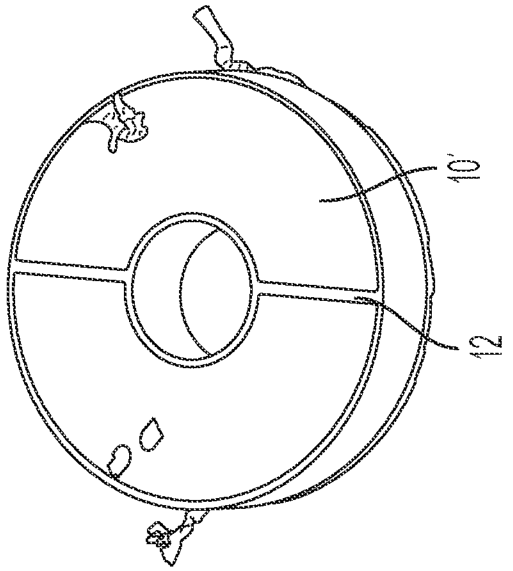
Figure 3G:
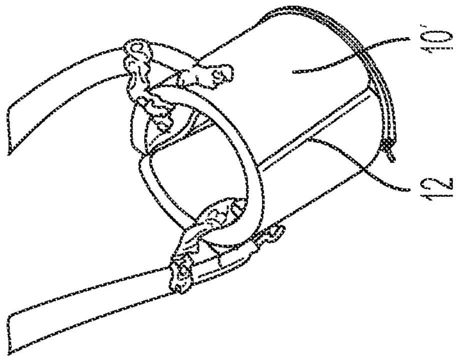
Figure 3F:
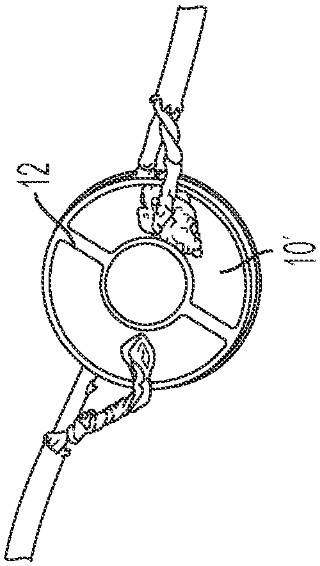

In some embodiments, the piezoelectric transducer 10 may be a hollow tube (e.g., a hollow cylindrical transducer that does not include the upper and lower planar walls), as shown in FIGS. 3A and 3C. The ultrasonic waves may be generated in a radial direction inside the tube, and the nodes thereof may form a series of concentric circles (as shown in the cured gel of FIG. 4B). A first open end of the hollow tube piezoelectric transducer may be placed against the sampling surface, and the rapidly curable liquid gel may be applied to the region of the sampling surface that is exposed within the inside of the hollow tube.

In some embodiments, the piezoelectric transducer may include one or more pairs of parallel plates. The paired plates may generate counter-propagating (traveling) ultrasonic waves parallel to the sampling surface, and a variable phase difference between the counter-propagating waves may be used to manipulate the analyte and/or metal particles into arbitrary positions with respect to the coordinate between the parallel plates. The parallel plates may be placed perpendicular to and against the sampling surface, and the rapidly curable liquid gel may be applied to the region of the sampling surface that is between the parallel plates.

In some embodiments, the piezoelectric transducer may include a plate and a concave reflector. The plate may generate a traveling wave parallel to the sampling surface and toward the concave reflector, and the position of the reflector with respect to the plate may be used to manipulate the analyte and/or metal particles into an intermediate position between the two. In some embodiments, the reflector may be in a fixed (pre-set) position so that the particles are manipulated into a corresponding fixed position with respect to the plate and reflector, but embodiments of the present disclosure are not limited thereto. In some embodiments, for example, the position of the reflector may be adjustable so that the positions of particles can be manipulated by varying the ultrasonic field in real time, prior to polymerization. The plate and concave reflector may be placed perpendicular to and against the sampling surface, and the rapidly curable liquid gel may be applied to the region of the sampling surface that is between the two parts of the transducer.

In some embodiments, the piezoelectric transducer may have the form of a solid polygon (e.g., a cylindrical disk) that is used to emit an acoustic beam toward a metal plate having a spiral or vortex-shaped design engraved on the side opposite the incident acoustic beam. The spiral design on the metal plate "shapes" the acoustic beam that is transmitted into the medium on the other side of the plate, and particles suspended in the medium may subsequently be localized in a spiral pattern similar to the design on the plate. In some embodiments, any engraved design capable of shaping the acoustic beam into a shape having one or more focal points may be used.

In some embodiments, as shown in FIGS. 3D through 3G, the piezoelectric transducer 10' may include one or more breaks 12. For example, the hollow tube piezoelectric transducer 10' may be a "split-ring" transducer including a plurality of breaks 12 in the circumference of the tube. The breaks 12 may be vertical (along the length of the tube), and in some embodiments may extend along the height of the tube (as shown best in FIGS. 3E and 3G). The term "break" as used herein to describe the structure of the piezoelectric transducer may refer to a region included with the body of the transducer that does not produce ultrasonic waves (for example, that is piezoelectrically or acoustically inactive, or not piezoelectric). The ultrasonic waves produced by the transducer may thus be further perturbed by the plurality of breaks due to the change in symmetry, possibly changing the number and positions of nodes and anti-nodes in the ultrasonic field, and hence the distribution or position of the aggregated analyte and metal particles. The number and position of the breaks is not particularly limited, but may be selected according to the desired number and distribution of nodes in the ultrasonic waves. In some embodiments, the piezoelectric transducer may include two, three, or four breaks, which may be symmetrically positioned along the width or along the circumference of the transducer (depending on the form of the transducer). In some embodiments, the breaks may be formed by slicing a single-bodied transducer into pieces and reassembling the pieces with a non-piezoelectric filler material (e.g., epoxy or the like), such that the break contains the non-piezoelectric filler material. In some embodiments, the breaks may be formed by stripping the transducer electrodes on both sides (e.g., through mechanical abrasion or chemical etching of the conductive electrode layer on the surface of the transducer) so that the portion of the piezoelectric transducer immediately between those stripped areas is not electrically activated. Stated another way, in some embodiments, the piezoelectric transducer may include two or more separately excited transducer portions (sources), connected via one or more piezoelectrically inactive breaks. In some embodiments, the separately excited transducer portions may be excited at different resonant mode frequencies (for example, differing by about 10 Hz to 100 Hz) and/or at different phases (for example, differing by about $\pi/10$ to about $\pi/4$) to thereby provide finer control of the co-aggregation of analyte and metal particles.

The ultrasonic waves may be generated and applied for any suitable duration (time) needed to achieve the aims described above. In some embodiments, for example, the ultrasonic waves may be applied for about 5 seconds to about 60 seconds. Those having ordinary skill in the art are capable of selecting a suitable duration of application. However, in some embodiments, the ultrasonic waves may be applied for the duration of the curing, i.e., the ultrasonic waves may be applied for the same duration as the application of energy (e.g., UV radiation) for curing the rapidly curable liquid gel, such that the application of ultrasonic waves and the application of energy for curing are conducted simultaneously for the same duration.

In some embodiments, as discussed above, the ultrasonic waves may be applied to the rapidly curable liquid gel during curing, for example, while the gel is semi-liquid or in an intermediate state of curing. For example, the ultrasonic waves may be simultaneously or concurrently applied while a second form of energy (e.g., thermal, light, RF, etc.) is applied, for example by the portable device to enable rapid curing of the rapidly curable liquid gel. The applications may be entirely concurrent, or may overlap (e.g., be partially concurrent).

The piezoelectric transducer used to generate the ultrasonic waves may be connected to an excitation source and/or a power amplifier to power and control the transducer. Those having ordinary skill in the art are capable of selecting suitable control modules for the piezoelectric transducer.

In some embodiments, the transducer may also function to define the area of application of the gel, and thus maintain the gel in place over the desired portion of the sampling surface. For example, the transducer may be applied to the sampling surface so that the area of the sampling surface within the area or cavity circumscribed by the transducer (e.g., within the hollow ring, between plates and/or reflectors, etc.) can be filled with the rapidly curable liquid gel, and the transducer serves as a barrier such that the gel does not spread past the perimeter defined by the transducer.

The energy type and the corresponding portable device to enable rapid curing of the rapidly curable liquid gel may each be selected according to the properties of the liquid gel. In some embodiments, for example, when the rapidly curable liquid gel is cured by UV irradiation, the portable device to enable rapid curing of the rapidly curable liquid gel may be a handheld UV lamp or laser. The wavelength of the portable device to enable rapid curing may be selected to match the light absorption wavelength of a photoinitiator for cross-linking within the rapidly curable liquid gel. In some embodiments, the UV lamp may be a commonly available lamp e.g., having a wavelength in the UV spectrum (i.e., 100 to 400 nm, for example, about 254 nm, 365 nm, etc.). The portable device may be applied for any duration sufficient to ensure substantially complete polymerization, or for example, formation of a stable sampling matrix that can be separated from the sampling surface as a single piece. In some embodiments, for example, the portable device may be applied for about 5 seconds to about 60 seconds, for example, about 10 seconds to about seconds.

When the ultrasonic field and the portable device for rapid curing are applied in series and/or concurrently applied to the rapidly curable liquid gel, the analyte and metal particles can be co-aggregated and "frozen" in selected regions of high concentration within the resulting polymerized sampling matrix. These regions of high concentration, as defined above, can then be analyzed using a Raman spectrometer.

Any suitable method or device may be used to detect Raman scattering of the sampling matrix. In some embodiments, the Raman spectrometer may be a standard laboratory Raman microscope. In some embodiments, the Raman spectrometer may be a handheld Raman device, enabling non-destructive read out analyses of traces of Raman active material in the field. The Raman laser may be applied to regions of high concentrations, including nodes of the previously applied ultrasonic waves, locations corresponding to cracks in the sampling surface, etc.

The portable or handheld Raman device may be any suitable such device, without limitation. In some embodiments, for example, the portable Raman device may include a portable Raman laser. The cured sample may be interrogated by different excitation laser wavelengths to increase the signal or limit fluorescence of the sample. Those of ordinary skill in the art would be able to determine an appropriate wavelength to use. However, in some embodiments, the portable Raman device may include a portable excitation laser with an excitation wavelength of 532 nm, 780 nm or 1064 nm. One non-limiting example of a suitable handheld Raman device is the THERMO SCIENTIFIC™ FIRSTDEFENDER™ RMX Handheld Chemical Identification Analyzer (ThermoFisher Scientific, Waltham, MA).

Some embodiments may further include a Raman probe. In some embodiments, the Raman probe may be a Raman-active label or tag, which may bind to or form a complex with materials that are normally Raman inactive, subsequently providing a characteristic Raman shift that can be detected in lieu of directly detecting the Raman inactive material. In some embodiments, the Raman probe may further enhance the Raman signal of an analyte, for example, by associating with (e.g., co-localizing, absorbing to, covalently bonding with, and/or forming a charged complex with) one or more metal particles and/or analyte molecules to promote co-aggregation and formation of Raman hot spots.

In some embodiments, the Raman probe may be or include a Raman-inactivating material. Stated another way, the Raman probe may quench (e.g., at least partially decrease or depress) the Raman fluorescence of a material, for example when the Raman probe is adsorbed, bonded to, or complexed with the material. In some embodiments, the Raman-inactivating material may selectively quench the rapidly curable liquid gel to thereby decrease the background fluorescence of the sample. In some embodiments, the Raman-inactivating material may selectively associate with and quench one or more analytes, enabling confirmation of an analyte's presence when the quenched and non-quenched samples are compared.

In some embodiments, the Raman probe may be or include a material that acts as a Raman tag (e.g., is fluorescent) in the absence of a particular analyte, but becomes Raman inactive in the presence of that analyte, due to e.g., complex dissociation, ligand exchange, etc. For example, the Raman probe may be or include a Raman-active organic ligand complexed with one or more SERS-enhancing metal particles, and preferential binding of the organic ligand to a metal ion analyte of interest may thereby result in quenching of the previously SERS-enhanced signal for the organic ligand. However, embodiments of the present disclosure are not limited thereto, and the Raman probe may rely on other types of chemical transformations to trigger quenching.

In some embodiments, the Raman probe may be included in the rapidly curable liquid gel prior to polymerization. In some embodiments, the Raman probe may be applied, added to, or otherwise used to treat the polymerized sampling matrix prior to or during Raman analysis.

Raman probes have been used to localize and identify biological agents such as proteins, DNA, and virotoxins. Non-limiting examples of Raman probes, targets thereof, and methods of using and interpreting such probes are described in Li, Y. et al., "Raman tags: Novel optical probes for intracellular sensing and imaging," Biotechnology Advances, 2017, 3, 168-177, the entire content of which is incorporated herein by reference. In addition, an example Raman probe scheme involving quenching is described in e.g., Du, Y. et al., "Surface-Enhanced Raman Scattering Chip for Femtomolar Detection of Mercuric Ion (II) by Ligand Exchange," *Analytical Chemistry,* 2013, 85(6), 3160-3165, the entire content of which is incorporated herein by reference.

A method according to embodiments of the present disclosure includes: applying the rapidly curable liquid gel to the sampling surface; co-aggregating one or more metal particles in the rapidly curable liquid gel and an analyte from (on or in) the sampling surface; curing the rapidly curable liquid gel to yield a sampling matrix including the analyte; and removing the sampling matrix including the analyte from the sampling surface. According to some embodiments, co-aggregating the metal particles and analyte includes, for example, applying ultrasonic waves generated by the piezoelectric transducer to the rapidly curable liquid gel and underlying sampling surface, thereby co-aggregating the metal particles and analyte. In some embodiments, curing the rapidly curable liquid gel may be at least partially concurrent with co-aggregation of the metal particles and analyte. The rapidly curable liquid gel, metal particles, piezoelectric transducer, methods of co-aggregation, sampling matrix, and methods of applying or manipulating these elements may be the same as described above.

EXAMPLES

The following Examples and Comparative Examples are provided for illustrative purposes only, and are not to be construed as limiting the embodiments of the present disclosure.

Example Ultrasonic Fields

An ultrasonic field was generated using a continuous sine wave having an amplitude of 70-100 mV with 50 dB gain (total voltage of 23.3-33.3 V) at a frequency of 1.080±0.01 MHz and applied to various rapidly cured liquid gel samples.

Comparison of Sampling Rates by Base Technique (without Ultrasonic Field)

Figure 1B:
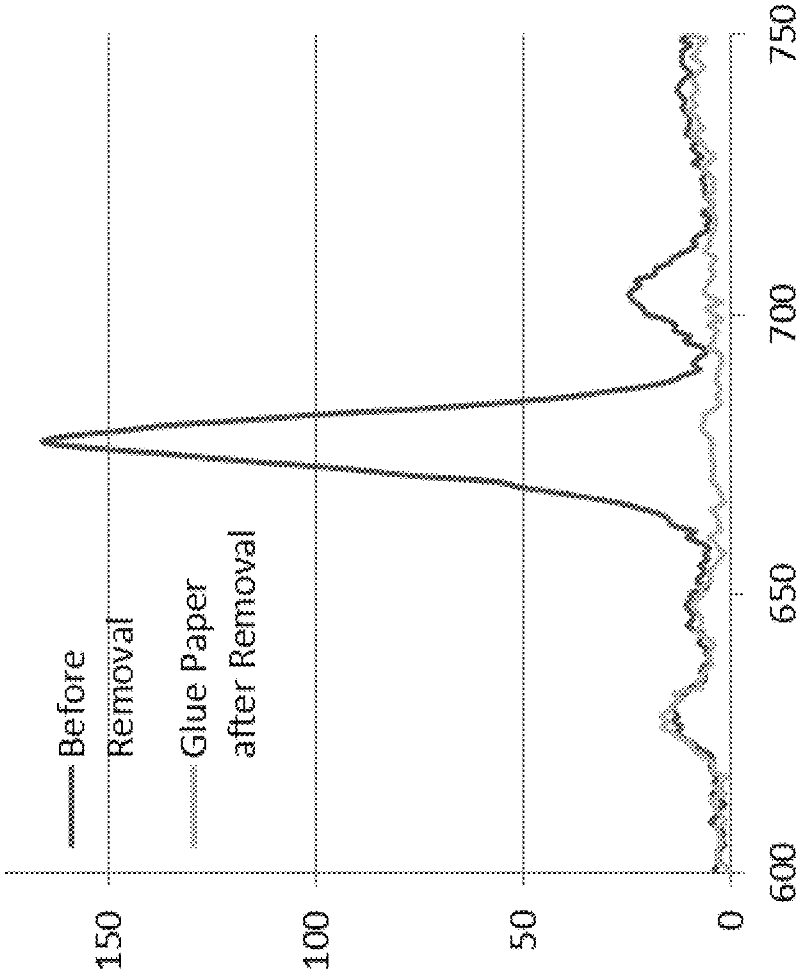
FIG. 1B is a graph comparing the analyte concentration in the crack depicted in FIG. 1A (left) both before (i.e., within the crack) and after removal using the glue paper.
Figure 1C:
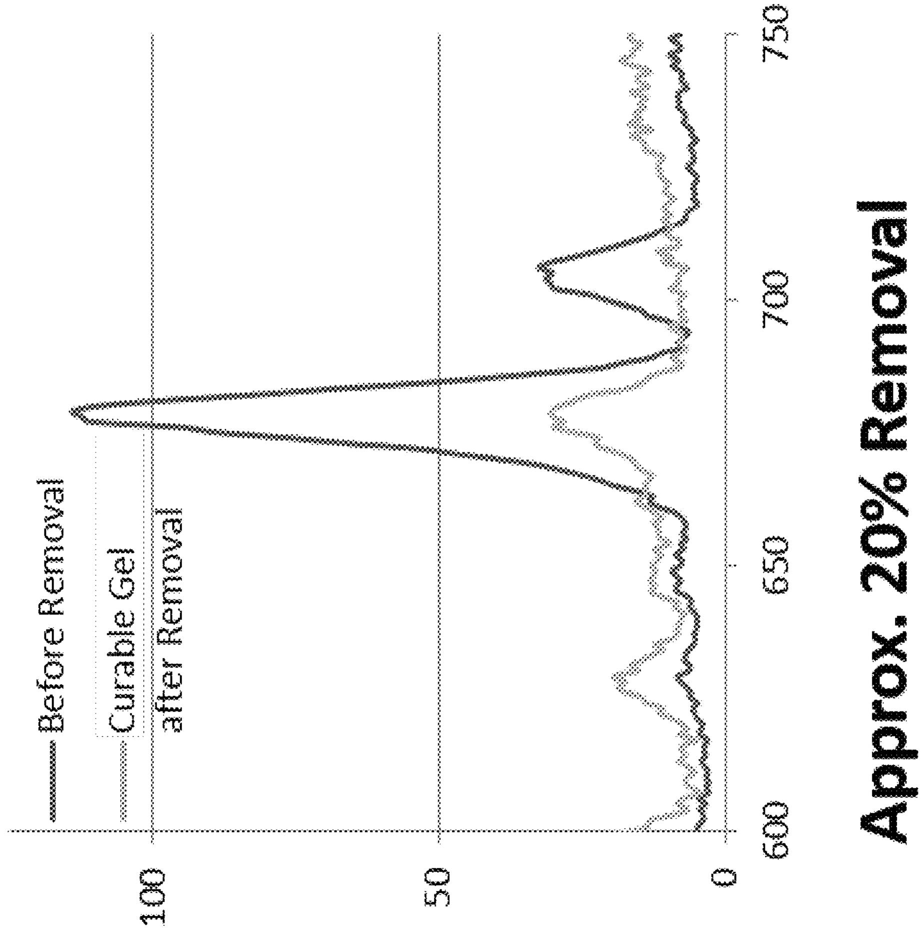
FIG. 1C is a graph comparing the analyte concentration in the crack depicted in FIG. 1A (right) both before (i.e., within the crack) and after removal using the rapidly curable gel according to embodiments of the present disclosure.

The efficacy of sampling using a rapidly curable liquid gel was compared to that of sampling using forensic glue paper. FIG. 1A is a schematic illustration comparing analyte sampling (collection) from a surface containing a trace amount of uranyl nitrate embedded in a crack in the surface, using glue paper (left) or the rapidly curable liquid gel according to embodiments of the present disclosure (right). FIGS. 1B and 1C depict the spectra of the glue paper (FIG. 1B) and the sampling matrix formed from the rapidly curable liquid gel (FIG. 1C). In FIGS. 1B and 1C, each spectrum trace overlays a control trace showing the characteristic spectrum of the analyte with a sampling trace of the analyte material collected from the surface. A negligible amount of analyte was collected using the glue paper, likely because the glue paper is not able to penetrate the crack and efficiently collect the analyte contained therein. In contrast, approximately 20% of the analyte present on the surface was collected using the rapidly curable liquid gel and its associated method of use.

Figure 2B:
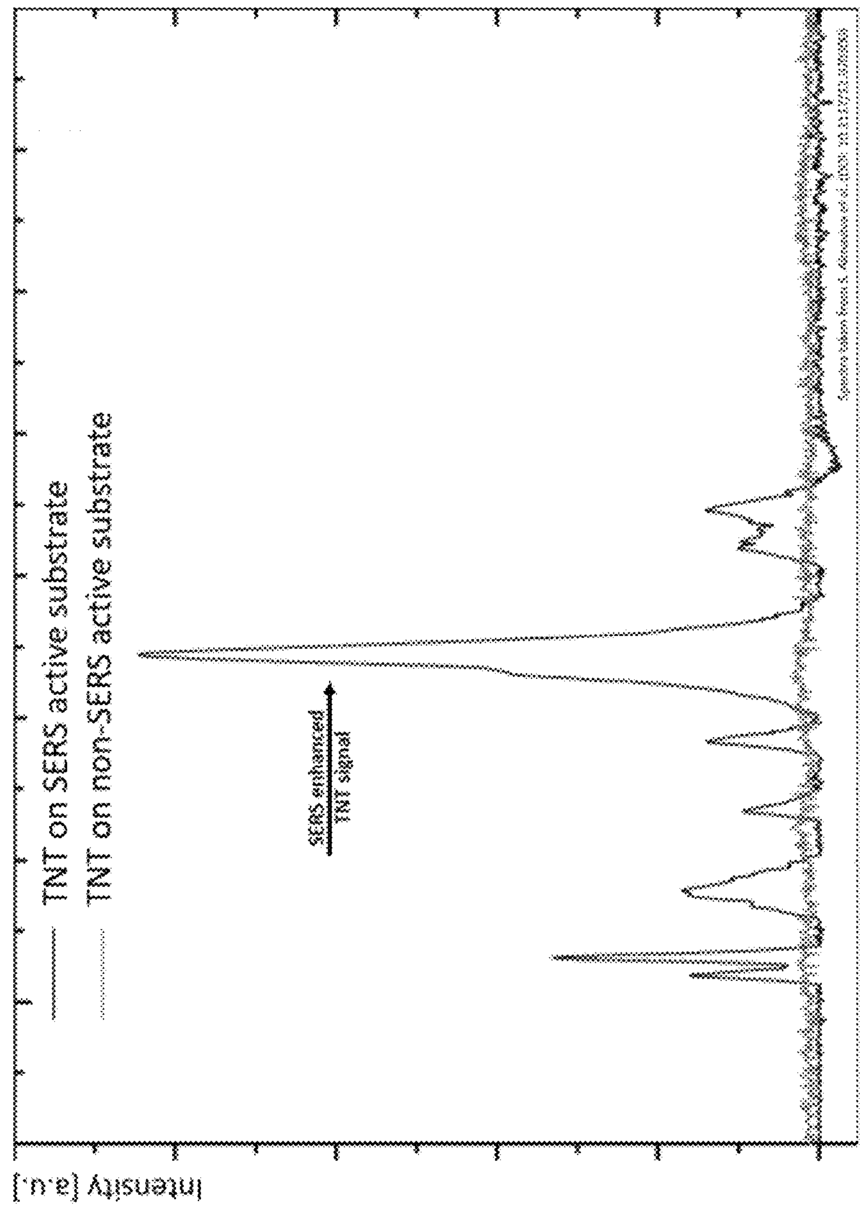
FIG. 2B is a composite spectral plot comparing the Raman scattering of a trinitrotoluene (TNT) sample on a SERS active substrate containing SERS enabling nanoparticles as depicted generally in the lower left schematic illustration of FIG. 2A, versus a non-SERS active substrate that does not include the nanoparticles as depicted generally in the upper schematic illustration of FIG. 2A, taken from Almaviva, S. et al., "Trace detection of explosives and their precursors by surface enhanced Raman spectroscopy," Proc. SPIE 8546, Optics and Photonics for Counterterrorism, Crime Fighting, and Defence VIII, 2012, 854602.
Figure 2A:
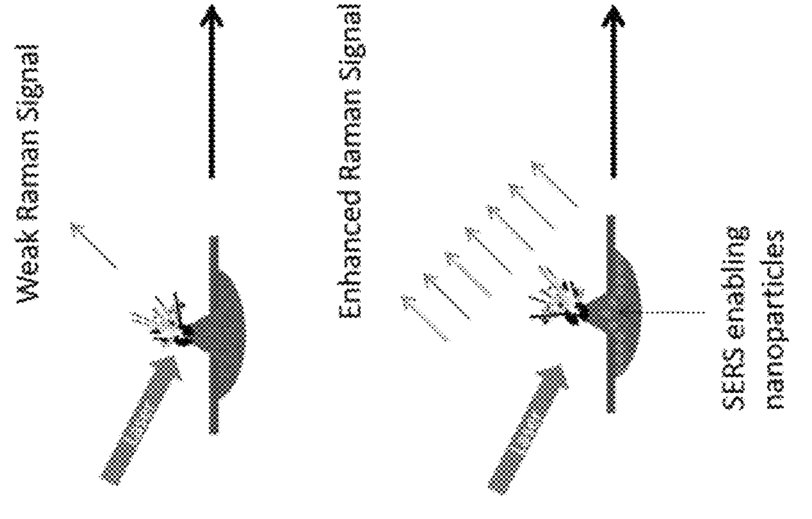
FIG. 2A is a schematic comparing the strength of Raman scattering on a SERS active substrate containing SERS enabling nanoparticles (lower schematic illustration), versus a non-SERS active substrate that does not include the nanoparticles (upper left schematic illustration), taken from Almaviva, S. et al., "Trace detection of explosives and their precursors by surface enhanced Raman spectroscopy," Proc. SPIE 8546, Optics and Photonics for Counterterrorism, Crime Fighting, and Defence VIII, 2012, 854602.

Comparison of Raman Signal with and without Enhancement by SERS Enabling Metal Particles FIG. 2A is a schematic illustration comparing Raman scattering on a SERS active substrate containing SERS enabling nanoparticles (lower schematic) to a non-SERS active substrate that does not include the nanoparticles (upper schematic). FIG. 2B is a composite spectral plot comparing the Raman scattering of a TNT sample on a SERS active substrate containing SERS enabling nanoparticles versus a non-SERS active substrate that does not include the nanoparticles, as reproduced from Almaviva, S. et al., "Trace detection of explosives and their precursors by surface enhanced Raman spectroscopy," Proc. SPIE 8546, Optics and Photonics for Counterterrorism, Crime Fighting, and Defence VIII, 2012, 854602, the entire content of which is incorporated herein by reference. The sample taken in the absence of SERS enabling nanoparticles shows almost no detectable signal, while the sample taken in the presence of SERS enabling nanoparticles shows distinctive Raman peaks. The comparison shows a clear enhancement of the TNT Raman fingerprint in the presence of the SERS enabling nanoparticles.

Example Components and Usage of the Kit for Collecting an Analyte from a Sampling Surface FIGS. 3A-C are schematics showing an example piezoelectric transducer having the shape of a hollow cylinder that can be placed against a surface to be sampled (FIG. 3A) and filled with the rapidly curable liquid gel. Here, the transducer is placed against a glass slide that has been exposed to a solution of a cerium oxide ($CeO_2$) mixed into an aliquot of rapidly curable liquid gel, which solution was added to the center cavity of the piezoelectric transducer. A portable handheld UV lamp (pocket UV lamp) for curing the rapidly curable liquid gel is shown for scale (FIG. 3B) compared to an American quarter coin, and was used to irradiate the rapidly curable liquid gel within the transducer (FIG. 3C).

Figure 4B:
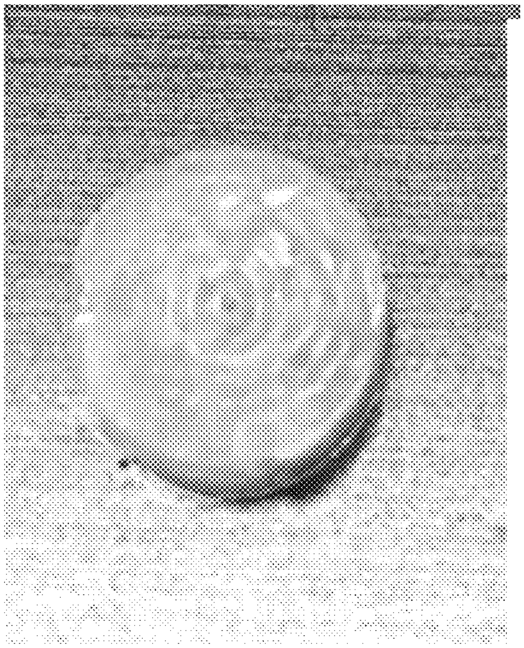
FIG. 4B is a photographic image of an example polymeric sampling matrix produced by curing a rapidly curable liquid gel according to embodiments of the present disclosure while concurrently (simultaneously) applying ultrasonic waves.
Figure 4A:
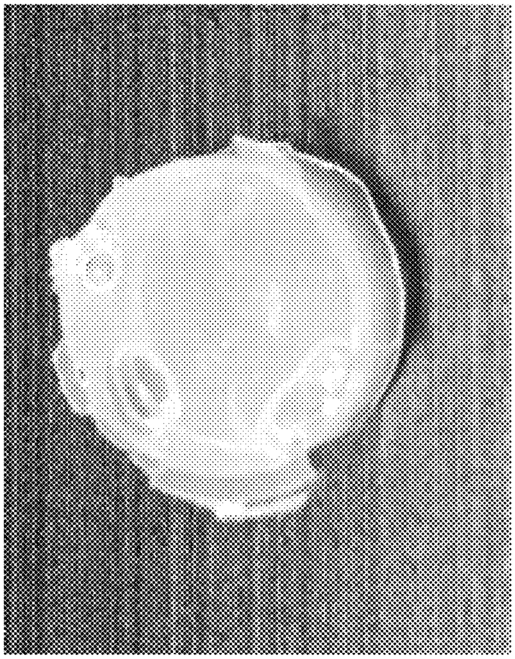
FIG. 4A is a photographic image of an example polymeric sampling matrix produced by curing a rapidly curable liquid gel according to embodiments of the present disclosure without applying ultrasonic waves.

FIG. 4A is a photographic image of an example sampling matrix produced by curing the rapidly curable liquid gel without applying ultrasonic waves. FIG. 4B is a photographic image of an example sampling matrix produced by applying ultrasonic waves alone to the rapidly curable liquid gel for an initial 5 seconds, then concurrently (simultaneously) irradiating the gel with the portable handheld UV lamp for about 20 seconds. The images show the "bottom" surfaces of the films that were adjacent to the glass slide sampling surface of FIGS. 3A and 3C. The concentric rings in the sampling matrix of FIG. 4B are the result of the piezoelectric transducer being applied to the rapidly curable liquid gel before and during curing, and reflect the acousto-mechanical energy waveforms applied to the liquid gel. In contrast, the sampling matrix of FIG. 4A, which was not treated with ultrasonic waves, does not include these rings.

Figure 5:
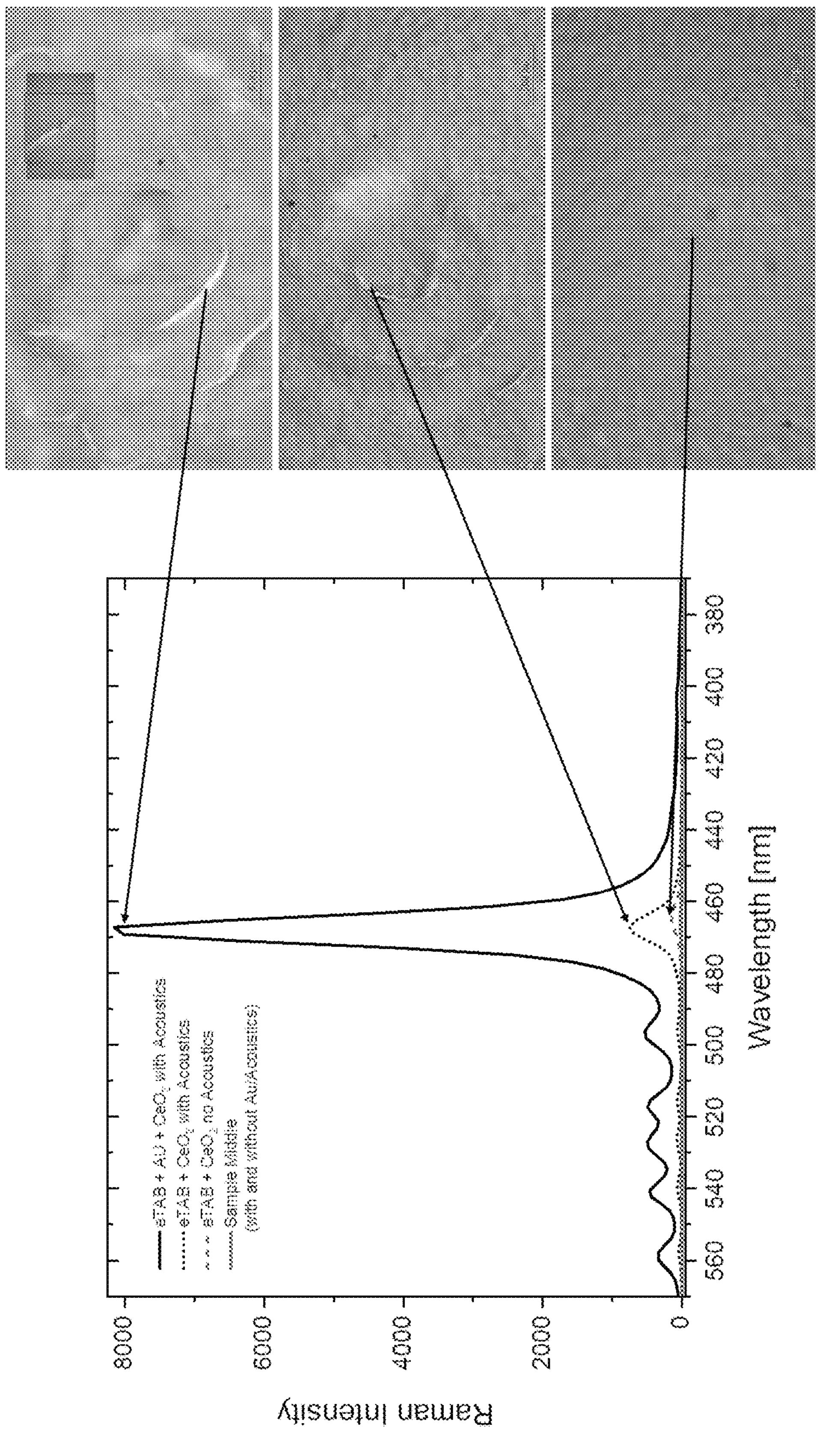
FIG. 5 is a composite spectral plot comparing the Raman scattering of the surface of $CeO_2$ samples at the indicated points (+), including a sample collected without nanoparticles and without applying ultrasound (lower right photo); a sample collected without nanoparticles while applying ultrasound (center right photo); and a sample including nanoparticles, collected while applying ultrasound (e.g., as in FIG. 4B) (upper right photo); and the Raman spectra taken at the cross-sectional middle of the samples (e.g., away from the surface) which showed no identifiable signal peaks, regardless of nanoparticle inclusion/omission or ultrasound application/omission (bottom-most, light gray trace)

FIG. 5 is a composite spectral plot comparing the Raman scattering of the surface of samples similar to those shown in FIGS. 4A and 4B, as collected on $CeO_2$-containing glass slides as in FIGS. 3A to 3C, and analyzed at the indicated points (+). Included are a sample collected without metal particles and without applying an ultrasonic field (lower right photo); a sample collected without metal particles while applying an ultrasonic field (center right photo); and a sample including 200 nm Au metal particles, collected while applying an ultrasonic field (e.g., as in FIG. 4B) (upper right photo). The Raman spectrum taken at the cross-sectional middle of each of the samples (e.g., away from the surface) showed no identifiable signal peaks, regardless of metal particle inclusion/omission or ultrasound application/omission (single representative line shown for clarity). The Raman spectrum of a sample surface that did not include Au metal particles (or any other metal particles) and was not exposed to ultrasonic waves showed the second lowest spectral response, corresponding to low detection of the $CeO_2$. The Raman spectrum of the sample surface that did not include Au metal particles (or any other metal particles) but was exposed to ultrasonic waves showed a slightly increased spectral response. The Raman spectrum of the sample surface including Au metal particles, which was additionally exposed to ultrasonic waves, provided the clearest and strongest Raman signal, demonstrating the clear benefits of using both metal particles and ultrasonic waves to increase detection efficiency by almost 3 orders of magnitude.

The peak heights and areas were calculated for various samples and normalized against the peak height and area of a reference sample that did not include metal particles. The results are shown in Table 1:

TABLE 1

| Compared samples | Peak height ratio | Peak area ratio |
|---|---|---|
| Ultrasound, no metal particles vs. no ultrasound, no metal particles | 759/157 = 4.8 | 4969/1047 = 4.7 |
| Ultrasound + metal particles vs. ultrasound, no metal particles | 8151/759 = 11 | 55253/4969 = 11 |
| Ultrasound + metal particles vs. no ultrasound, no metal particles | 8151/157 = 52 | 55254/1047 = 53 |

As shown in Table 1, ultrasound (ultrasonic waves) alone provided a moderate increase in Raman signal (first entry). The combination of ultrasound and metal particles provided an even larger increase over ultrasound with no metal particles (second entry), as well as no ultrasound and no metal particles (third entry).

Comparison of Raman Scattering from Surface Vs. Within Polymer Matrix

Figure 6:
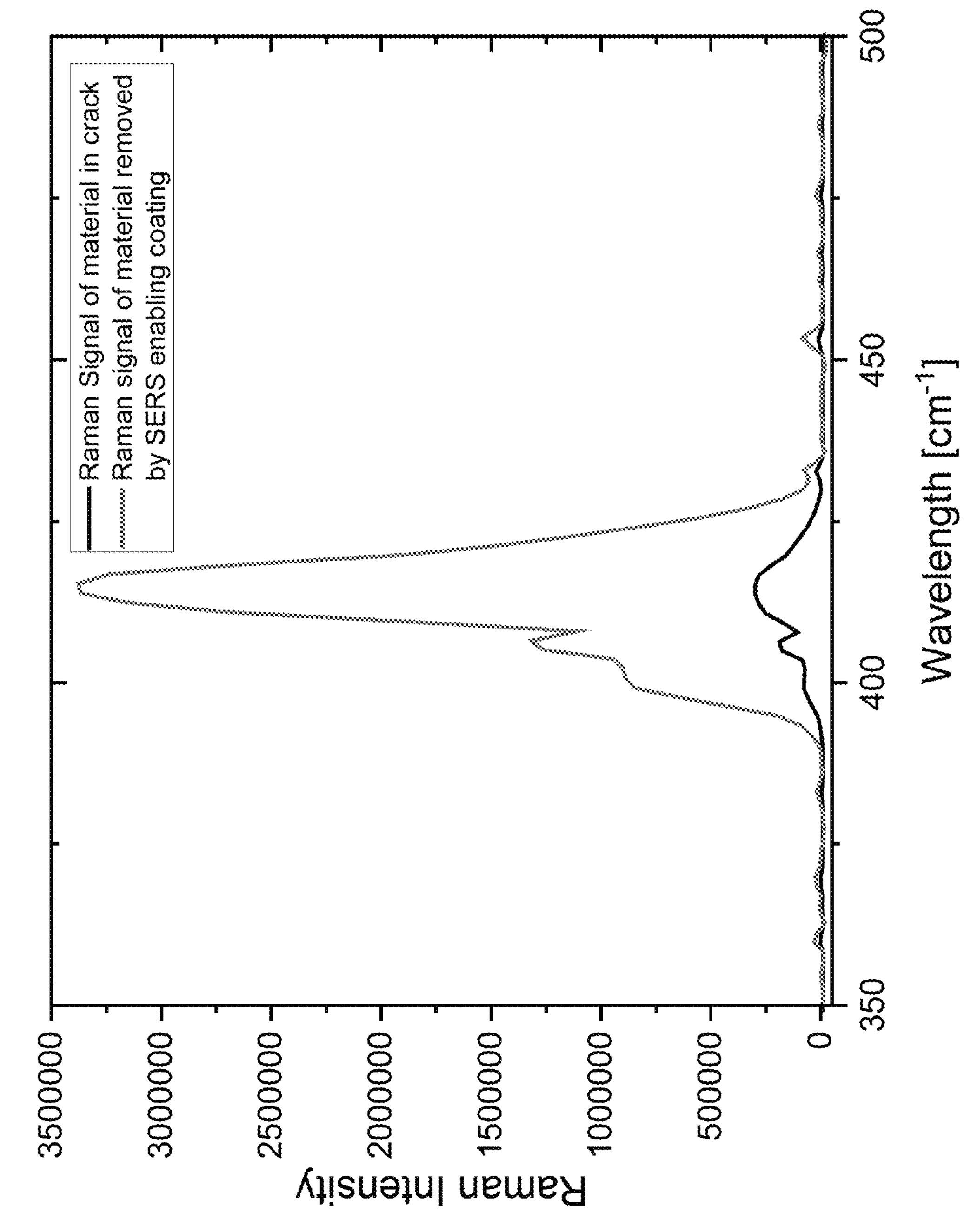
FIG. 6 is a spectral plot comparing the Raman scattering measured by a hand-held Raman device of a $CeO_2$ material measured in a crack to the Raman scattering measured by the hand-held Raman device of approximately 20% of the material removed and embedded in a SERS enabling polymer matrix (rapidly curable gel with Au metal particles aggregated using an acoustic transducer, and cured with UV) according to embodiments of the present disclosure, showing that even though only a small portion of the material is removed by the polymer matrix according to embodiments of the present disclosure, the signal of the targeted material is increased by an order of magnitude.

FIG. 6 is a spectral plot comparing the Raman scattering measured by a hand-held Raman device (i.e., the THERMO SCIENTIFIC™ FIRSTDEFENDER™ RMX Handheld Chemical Identification Analyzer (ThermoFisher Scientific, Waltham, MA)) of a material (i.e., $CeO_2$) measured in a crack on a substrate surface to the Raman scattering measured by the hand-held Raman device of the material removed by and embedded in a SERS enabling polymer matrix (rapidly curable gel with Au metal particles (300 nm particle size; concentration of about 4.5 E+9 particles/mL (10× concentrated)) aggregated using an acoustic transducer, and cured with UV irradiation) according to embodiments of the present disclosure. The rapidly curable liquid gel was co-aggregated using a cylindrical 10 mm diameter, unmodified transducer. And the settings for the acoustic assembly were 1.1 MHz and 110 mV, amplified by 50 dB and impedance matched with an RF tuner. Using the rapidly curable gel with the Au metal particles enabled collection of approximately 20% of the analyte from the surface crack.

As can be seen in the graph, even though only a small portion of the material (i.e., about 20%) is removed by the polymer matrix according to embodiments of the present disclosure, the signal of the targeted material is increased by an order of magnitude.

Comparison of Raman Scattering with and without Metal Particles

Figure 7:
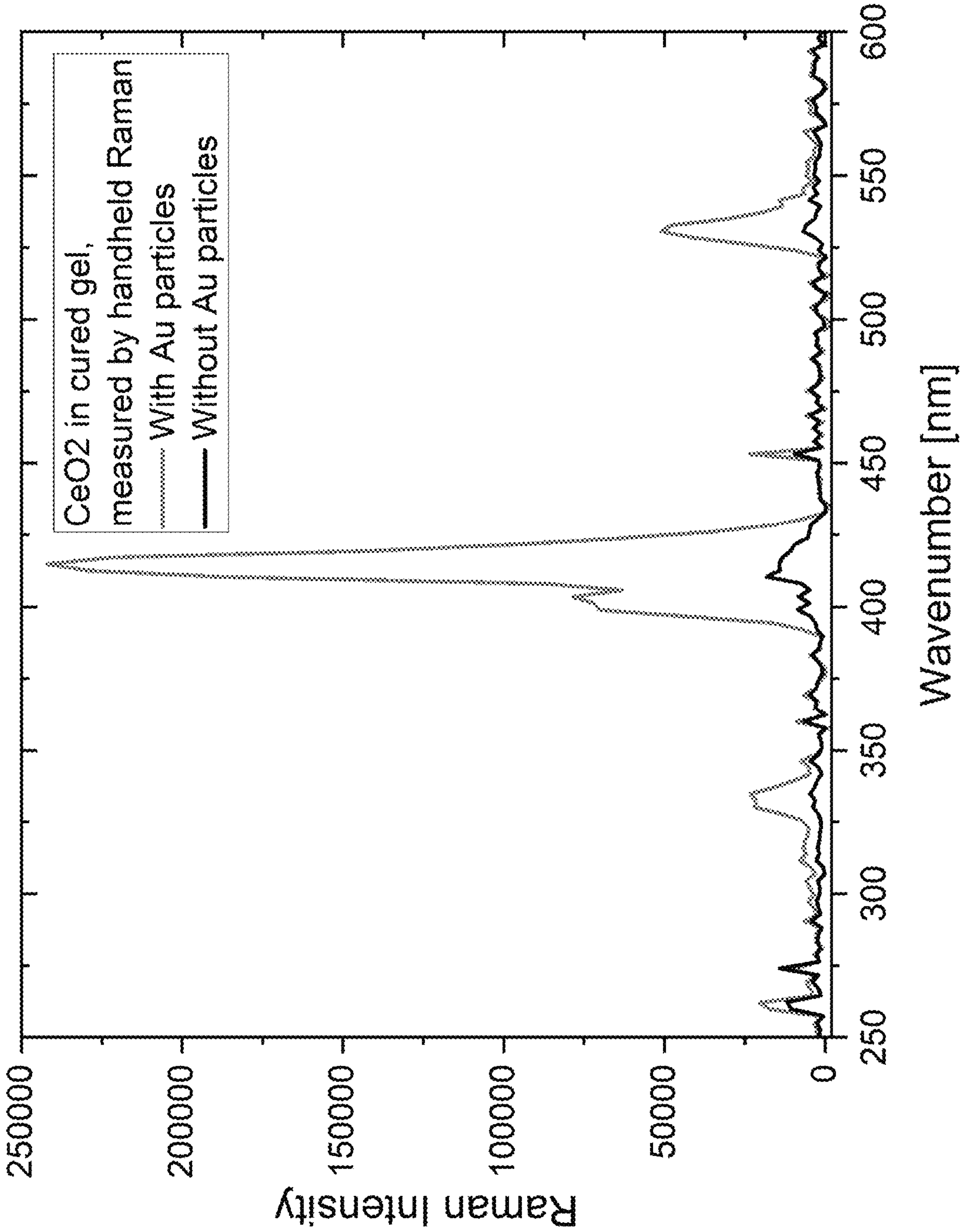
FIG. 7 is a spectral plot comparing the Raman scattering measured by a hand-held Raman device of the same amount of $CeO_2$ in a rapidly curable gel according to embodiments of the present disclosure without Au particles and with a concentration of 4.5 E+9 particles/mL (10× concentrated) Au particles having a particle size of 300 nm.

FIG. 7 is a spectral plot comparing the Raman scattering measured by a hand-held Raman device (i.e., the THERMO SCIENTIFIC™ FIRSTDEFENDER™ RMX Handheld Chemical Identification Analyzer (ThermoFisher Scientific, Waltham, MA)) of the same amount of $CeO_2$ in a rapidly curable gel according to embodiments of the present disclosure without Au particles and with Au particles (300 nm particle size; concentration of about 4.5 E+9 particles/mL (10× concentrated)). Prior to measurement by the hand-held Raman device, the rapidly curable liquid gels were subjected to ultrasound via a cylindrical 10 mm diameter, unmodified transducer, and irradiated with UV to effect curing of the polymer matrix. The settings for the acoustic assembly were 1.1 MHz and 110 mV, amplified by 50 dB and impedance matched with an RF tuner.

As can be seen from the graph, the inclusion of Au particles resulted in a significantly improved Raman intensity (i.e., a signal improvement of about an order of magnitude).

Comparison of Raman Scattering at Different Particle Sizes of Metal Particles

Figure 8:
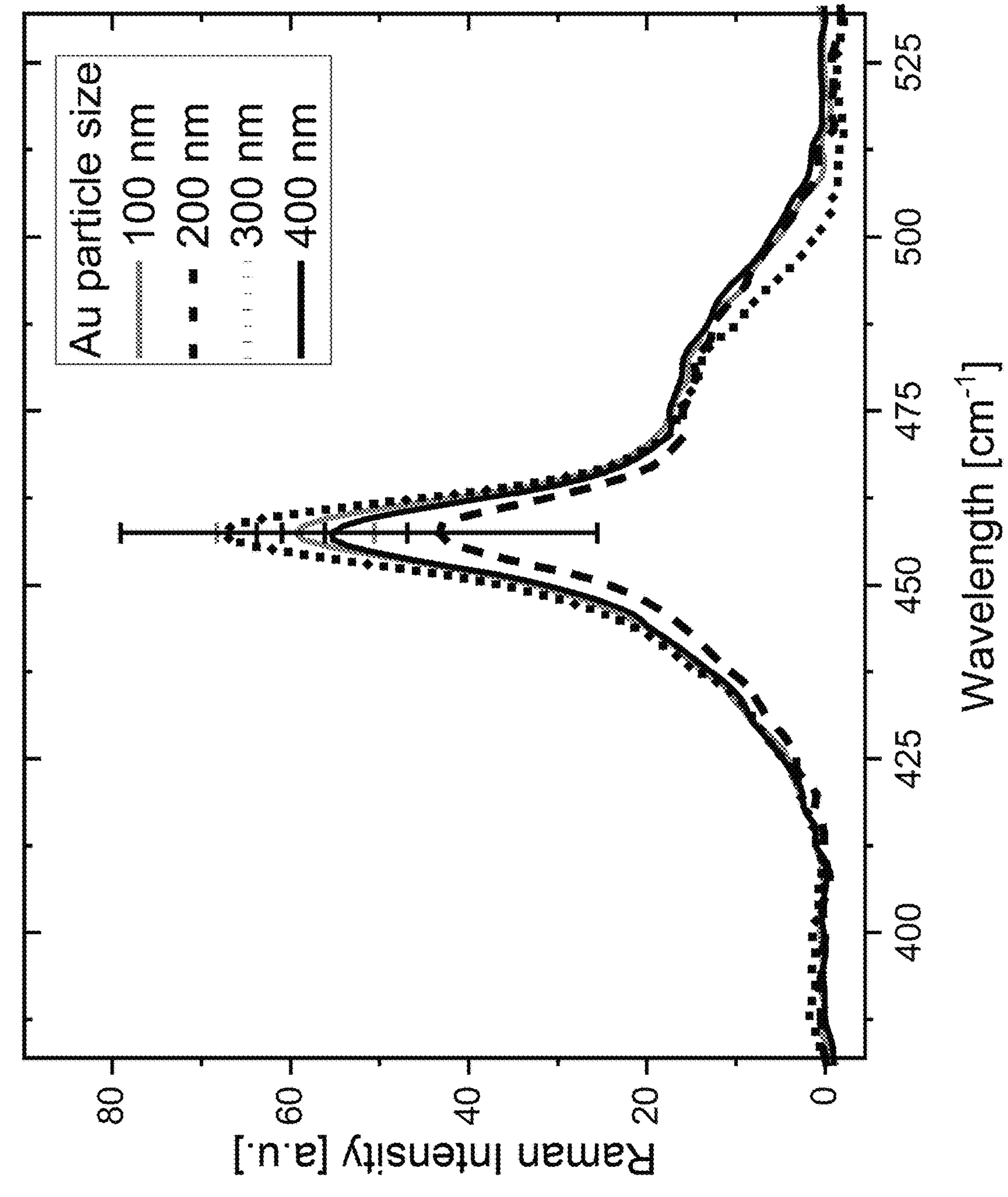
FIG. 8 is a spectral plot comparing the Raman scattering measured by a table-top Raman device of the same amount of $CeO_2$ in a rapidly curable gel according to embodiments of the present disclosure with the same concentration of Au particles but different particle sizes: 100 nm Au particles, 200 nm Au particles, 300 nm Au particles and 400 nm particles.

FIG. 8 is a spectral plot comparing the Raman scattering measured by a table-top Raman device of the same amount of $CeO_2$ (0.01 g $CeO_2$ per g of gel) in a rapidly curable gel according to embodiments of the present disclosure with the same concentration of Au particles (about 4.5 E+8 particles/mL (1×)) but different particle sizes. Specifically, FIG. 8 compares gels with 100 nm Au particles, gels with 200 nm Au particles, gels with 300 nm Au particles, and gels with 400 nm Au particles. Prior to measurement by the hand-held Raman device, the rapidly curable liquid gels were subjected to ultrasound via a cylindrical 10 mm diameter, unmodified transducer, and irradiated with UV to effect curing of the polymer matrix. The settings for the acoustic assembly were 1.1 MHz and 110 mV, amplified by 50 dB and impedance matched with an RF tuner.

As can be seen in the graph, while some small fluctuations in Raman intensity are observed between 100 nm and 400 nm, all of these particle sizes yield significantly improved Raman intensity. This significant improvement is particularly observable when compared with FIG. 7 showing the Raman intensity of gels that do not include any Au particles.

Figure 9:
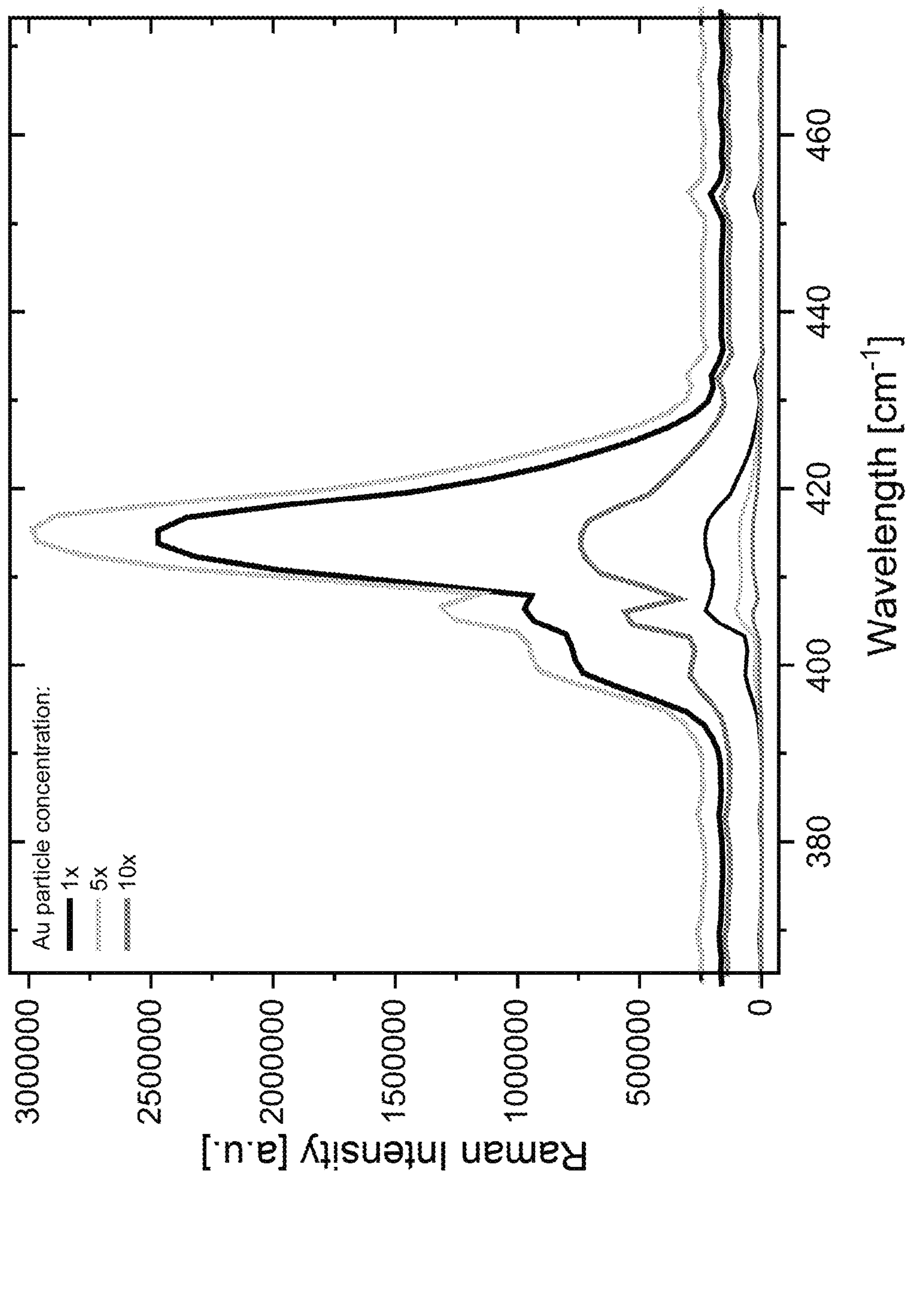
FIG. 9 is a spectral plot comparing the Raman scattering measured by a hand-held Raman device of the same amount of $CeO_2$ in a rapidly curable gel according to embodiments of the present disclosure with Au particles of the same particle size but having different concentrations of the Au particles: about 4.5 E+8 particles/mL (1×) Au particles, about 2.25 E+9 particles/mL (5× concentrated) Au particles, and about 4.5 E+9 particles/mL (10× concentrated) Au particles, where the thin lines in the graph (lower three traces) indicate the Raman intensity of the $CeO_2$ on the substrate before application, acoustic modification and curing of the rapidly curable liquid gel including the Au particles, and the thick lines (top three traces) indicate the Raman intensity of the $CeO_2$ within the cured matrix after removal.

Comparison of Raman Scattering at Different Concentrations of the Metal Particles FIG. 9 is a spectral plot comparing the Raman scattering measured by a hand-held Raman device (i.e., the THERMO SCIENTIFIC™ FIRSTDEFENDER™ RMX Handheld Chemical Identification Analyzer (ThermoFisher Scientific, Waltham, MA)) of the same amount of $CeO_2$ (0.01 g $CeO_2$ per g of gel) in a rapidly curable gel according to embodiments of the present disclosure with Au particles of the same particle size (300 nm) but having different concentrations of the Au particles: 4.5 E+8 particles/mL (1×) Au particles, 2.25 E+9 particles/mL (5× concentrated) Au particles, and 4.5 E+9 particles/mL (10× concentrated) Au particles. In the graph, the thin lines (lower three traces) indicate the Raman intensity of the $CeO_2$ on the substrate before application, acoustic modification and curing of the rapidly curable liquid gel including the Au particles. The thick lines (top three traces) indicate the Raman intensity of the $CeO_2$ within the cured matrix after removal. Prior to measurement by the hand-held Raman device, the rapidly curable liquid gels were subjected to ultrasound via a cylindrical 10 mm diameter, unmodified transducer, and irradiated with UV to effect curing of the polymer matrix. The settings for the acoustic assembly were 1.1 MHz and 110 mV, amplified by 50 dB and impedance matched with an RF tuner.

As can be seen in the graph, all concentrations of Au particles registered significant improvements in Raman intensity compared to measurements directly from the substrate (i.e., without the rapidly curable liquid gel). However, it can also be seen that the 1× and 5× concentrations of the Au particles register greater improvements in Raman intensity than the 10× concentration of Au particles.

Comparison of Raman Scattering at Different Excitation Wavelengths

Figure 10:
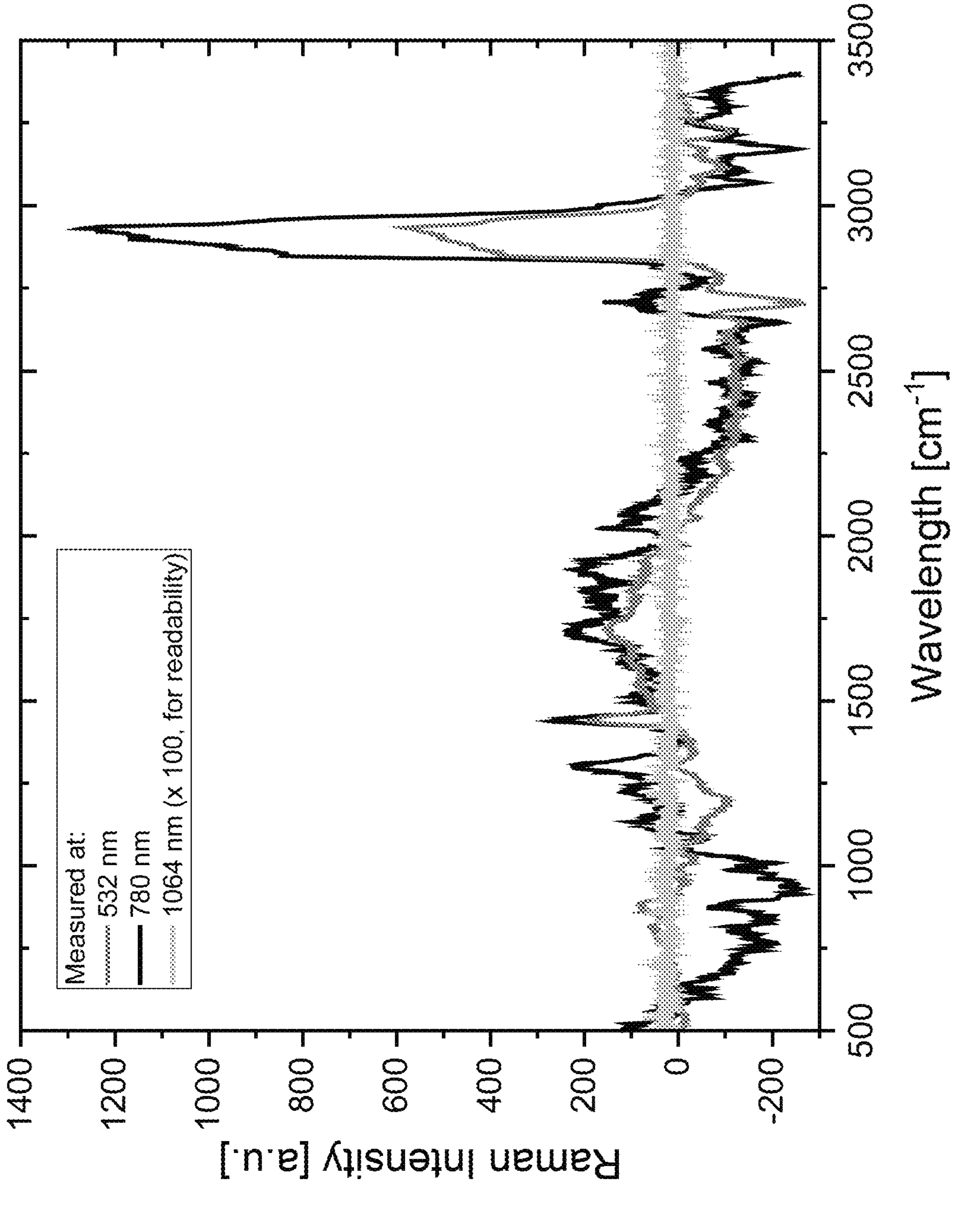
FIG. 10 is a spectral plot comparing the Raman scattering measured by a table-top Raman device of the same amount of $CeO_2$ in the same rapidly curable gel according to embodiments of the present disclosure, where the gels were measured by lasers with different excitation wavelengths.

FIG. 10 is a spectral plot comparing the Raman scattering measured by a table-top Raman device of the same amount of $CeO_2$ (0.01 g $CeO_2$ per g of gel) in the same rapidly curable gel according to embodiments of the present disclosure, where the cured gels were investigated with different laser excitation wavelengths. Specifically, the laser for sample interrogation had an excitation wavelength of 532 nm, 780 nm or 1064 nm. Prior to measurement by the table-top Raman device, the rapidly curable liquid gels were subjected to ultrasound via a cylindrical 10 mm diameter, unmodified transducer, and irradiated with UV to effect curing of the polymer matrix. The settings for the acoustic assembly were 1.1 MHz and 110 mV, amplified by 50 dB and impedance matched with an RF tuner.

As can be seen in the graph, while using a laser with an excitation wavelength of 532 nm or 780 nm generates good Raman intensity in the cured gel, using a laser with an excitation wavelength of 1064 nm generated an indeterminable Raman signal.

Embodiments described herein provide the possibility of using ordinary, widely available, and relatively inexpensive portable Raman spectrometers for quickly and accurately identifying trace amounts of CBRNE materials in-field. Such detection capabilities may have powerful relevance for threat analysis, law enforcement, and national security applications.

While certain exemplary embodiments of the present disclosure have been illustrated and described, those of ordinary skill in the art will recognize that various changes and modifications can be made to the described embodiments without departing from the spirit and scope of the present invention, and equivalents thereof, as defined in the claims that follow this description. For example, although certain components may have been described in the singular, i.e., “a” metal particle, “a” piezoelectric transducer, and the like, one or more of these components in any combination can be used according to the present disclosure. Additionally, although some embodiments are described as including a UV-curable rapidly curable liquid gel, it is understood that any rapidly curable rapidly curable liquid gel (e.g., being cured by some other energy input) may be used in place of the UV-curable counterparts.

Also, although certain embodiments have been described as "comprising" or "including" the specified components, embodiments "consisting essentially of" or "consisting of" the listed components are also within the scope of this disclosure. For example, while embodiments of the present invention are described as comprising applying the rapidly curable liquid gel to the sampling surface; co-aggregating one or more metal particles in the rapidly curable liquid gel and an analyte of the sampling surface; curing the rapidly curable liquid gel to yield a sampling matrix including the analyte; and removing the sampling matrix including the analyte from the sampling surface, embodiments consisting essentially of or consisting of these actions are also within the scope of this disclosure. Accordingly, a method of collecting an analyte from a sampling surface may consist essentially of applying the rapidly curable liquid gel to the sampling surface; aggregating one or more metal particles in the rapidly curable liquid gel and an analyte of the sampling surface; curing the rapidly curable liquid gel to yield a sampling matrix including the analyte; and removing the sampling matrix including the analyte from the sampling surface. In this context, "consisting essentially of" means that any additional components or process actions will not materially affect the results achieved by the method.

In addition, although example embodiments have been described as using an ultrasonic field and/or a piezoelectric transducer to manipulate and co-aggregate analyte and particles, it will be understood that other methods or phenomena, such as an electromagnetic field (as described in e.g., U.S. application Ser. No. 15/785,295 and U.S. Provisional Application No. 62/408,589, the entire content of each of which is incorporated herein by reference), may be used in addition to or in place of the ultrasonic field and/or a piezoelectric transducer to achieve co-aggregation.

As used herein, unless otherwise expressly specified, all numbers such as those expressing values, ranges, amounts or percentages may be read as if prefaced by the word "about," even if the term does not expressly appear. Further, the word "about" is used as a term of approximation, and not as a term of degree, and reflects the penumbra of variation associated with measurement, significant figures, and interchangeability, all as understood by a person having ordinary skill in the art to which this disclosure pertains. Any numerical range recited herein is intended to include all sub-ranges subsumed therein. Plural encompasses singular and vice versa. When ranges are given, any endpoints of those ranges and/or numbers within those ranges can be combined within the scope of the present disclosure. The terms "including" and like terms mean "including but not limited to," unless specified to the contrary.

Notwithstanding that the numerical ranges and parameters set forth herein may be approximations, numerical values set forth in the Examples are reported as precisely as is practical. Any numerical value, however, inherently contains certain errors necessarily resulting from the standard variation found in their respective testing measurements. The word "comprising" and variations thereof as used in this description and in the claims do not limit the disclosure to exclude any variants or additions.

What is claimed is:

1. A method comprising:

applying a rapidly curable liquid gel to a sampling surface, the rapidly curable liquid gel comprising one or more metal particles;

co-aggregating the one or more metal particles in the rapidly curable liquid gel and an analyte from the sampling surface by applying ultrasonic waves to the rapidly curable liquid gel and the sampling surface using a piezoelectric transducer;

curing the rapidly curable liquid gel to yield a sampling matrix including the analyte; and removing the sampling matrix including the analyte from the sampling surface.

2. The method of claim 1, wherein the curing the rapidly curable liquid gel is at least partially concurrent with the co-aggregating the one or more metal particles and the analyte.

3. The method of claim 1, wherein the piezoelectric transducer comprises a hollow tube and generates ultrasonic waves in a radial direction inside the hollow tube.

4. The method of claim 1, wherein the one or more metal particles has an average size of about 1 nm to about 400 nm.

5. The method of claim 1, wherein the one or more metal particles comprises gold (Au), silver (Ag), or any combination thereof.

6. The method of claim 1, wherein the rapidly curable liquid gel further comprises a Raman probe to co-localize with the one or more metal particles or the analyte.

7. The method of claim 1, wherein the rapidly curable liquid gel further comprises a Raman probe to associate with and quench the analyte.

8. The method of claim 1, wherein the rapidly curable liquid gel further comprises a Raman probe that is quenched in the presence of the analyte.

9. The method of claim 1, wherein the one or more metal particles comprise metal nanoparticles or metal nanostructures.

10. The method of claim 1, wherein the curing the rapidly curable liquid gel comprises using a portable energy source to deliver energy suitable to cure the rapidly curable liquid gel.

11. The method of claim 1, wherein the concentration of the one or more metal particles in the rapidly curable liquid gel is about 0.001 wt % to about 10 wt % with respect to the total weight of the rapidly curable liquid gel.

12. The method of claim 1, further comprising measuring a Raman intensity of the analyte in the sampling matrix after removing the sampling matrix containing the analyte from the sampling surface.

13. The method of claim 12, wherein the measuring the Raman intensity of the analyte comprises using a handheld Raman device.

14. A method comprising:

applying a rapidly curable liquid gel to a sampling surface;

aggregating an analyte of the sampling surface by applying ultrasonic waves to the rapidly curable liquid gel and the sampling surface using a piezoelectric transducer;

curing the rapidly curable liquid gel to yield a sampling matrix including the analyte; and removing the sampling matrix including the analyte from the sampling surface.

15. The method of claim 14, wherein the piezoelectric transducer comprises a hollow tube and generates ultrasonic waves in a radial direction inside the hollow tube.

16. The method of claim 14, wherein the curing the rapidly curable liquid gel comprises using a portable energy source to deliver energy suitable to cure the rapidly curable liquid gel.

17. The method of claim 14, further comprising measuring a Raman intensity of the analyte in the sampling matrix after removing the sampling matrix containing the analyte from the sampling surface.

18. The method of claim 17, wherein the measuring the Raman intensity of the analyte comprises using a handheld Raman device.

* * * * *